United States Patent [19]
Clements et al.

[11] Patent Number: 5,127,517
[45] Date of Patent: Jul. 7, 1992

[54] SYSTEM FOR STORAGE AND CARING FOR CONTACT LENSES

[75] Inventors: Donald A. Clements, Arlington; Michael J. Kent; William A. Fronk, both of Fort Worth, all of Tex.

[73] Assignee: Alcon Laboratories, Inc., Fort Worth, Tex.

[21] Appl. No.: 478,427

[22] Filed: Feb. 12, 1990

Related U.S. Application Data

[63] Continuation-in-part of Ser. No. 235,589, Aug. 24, 1988, Pat. No. 4,905,819.

[51] Int. Cl.⁵ .............................................. A45C 11/04
[52] U.S. Cl. ..................................... 206/5.1; 134/137; 222/207
[58] Field of Search ................... 206/5.1; 134/24, 34, 134/137; 222/207, 211

[56] References Cited

U.S. PATENT DOCUMENTS

| | | | |
|---|---|---|---|
| 2,940,589 | 6/1960 | Silverman | 206/5 |
| 3,054,412 | 9/1962 | Nickell | 134/137 |
| 3,113,579 | 12/1963 | Willis | 134/145 |
| 3,124,240 | 3/1964 | Croan | 206/5 |
| 3,326,358 | 6/1967 | Singleton | 206/5 |
| 3,460,552 | 8/1969 | Sturgeon | 134/135 |
| 3,473,886 | 10/1969 | Leeds | 21/91 |
| 3,623,492 | 11/1971 | Frantz | 134/143 |
| 3,705,668 | 12/1972 | Schwartzman | 222/207 |
| 3,856,571 | 12/1974 | Sherman | 134/34 |
| 4,036,357 | 7/1977 | Czelen | 206/5.1 |
| 4,077,547 | 3/1978 | Donoghue | 222/207 |
| 4,089,552 | 5/1978 | Hermanson | 294/1 CA |
| 4,106,673 | 8/1978 | Donoghue | 222/207 |
| 4,429,786 | 2/1984 | Hucal | 206/5.1 |
| 4,444,307 | 4/1984 | Jermyn | 206/5.1 |
| 4,776,360 | 10/1988 | Shih | 134/140 |
| 4,905,819 | 3/1990 | Clements et al. | 134/137 |

Primary Examiner—David T. Fidei
Attorney, Agent, or Firm—Zarley, McKee, Thomte, Voorhees & Sease

[57] ABSTRACT

A means, and system for storing and caring for contact lenses, including cleaning, rinsing, storing, disinfecting, lubricating, etc., including a self-contained contact lens holder to support and contain one or more contact lenses. A fluid conduit is associated with the contact lens holder to provide a pathway for fluid to the chamber or chambers holding each contact lens. A fluid container holding a fluid used in contact lens care can be put in fluid communication with the fluid conduit and is operable to selectively introduce fluid into the fluid conduit and fill the contact lens holder with the fluid. The contact lens holder, fluid conduit, and fluid container may all be incorporated in a unitary body, or fluid container and/or the fluid conduit can be selectively attachable to the contact lens holder so that different fluid containers can be interchangeable to the contact lens holder. In another aspect of the invention, the fluid container can be directly dispensed externally by passing the fluid through a dispensing tip instead of to the contact lens holder. The dispensing tip can either be incorporated in the contact lens holder or with respect to the fluid container.

33 Claims, 10 Drawing Sheets

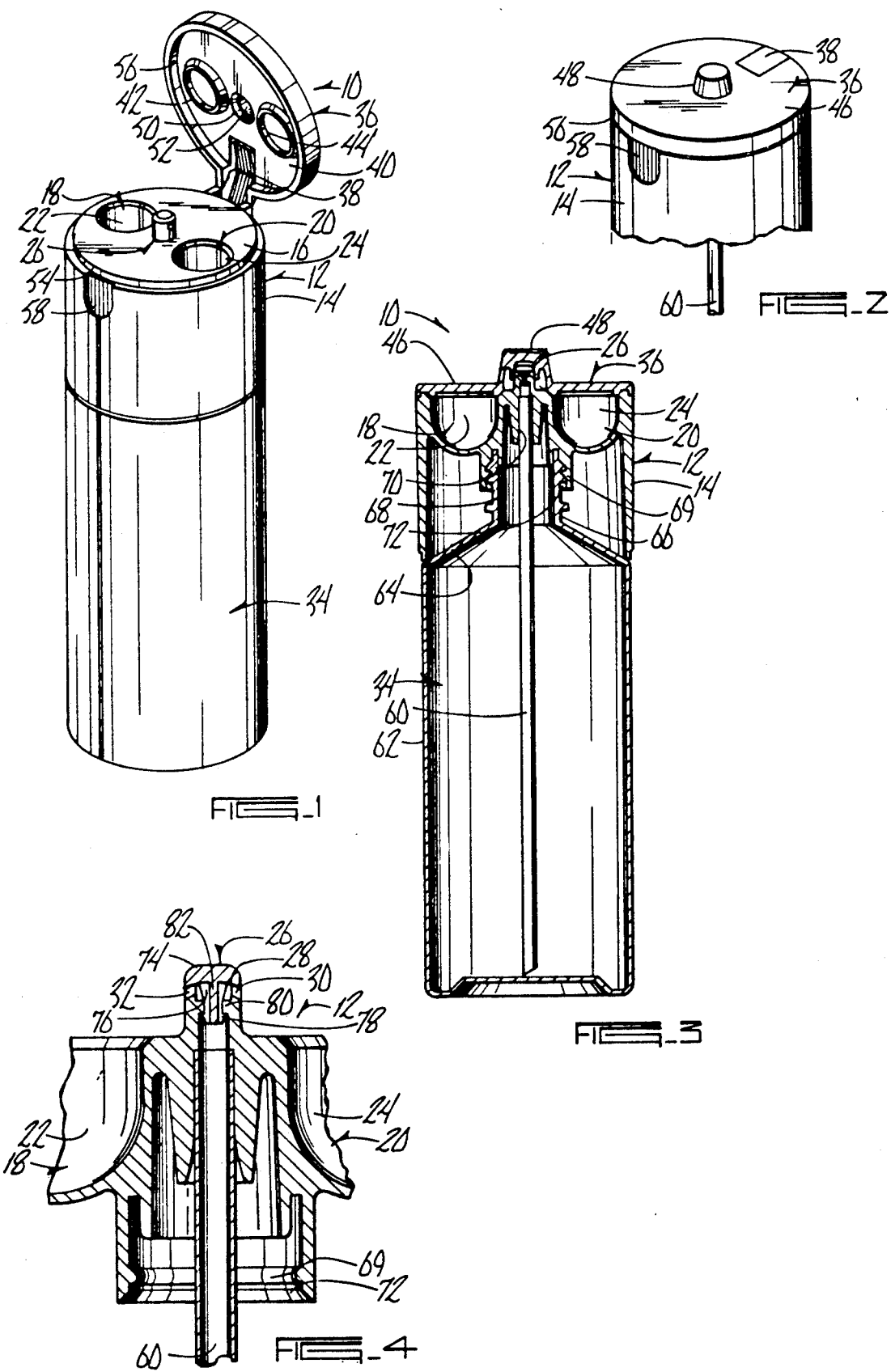

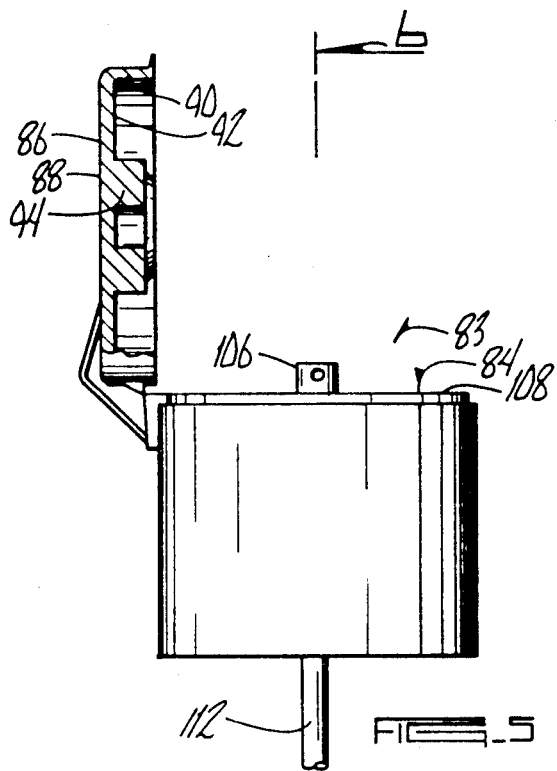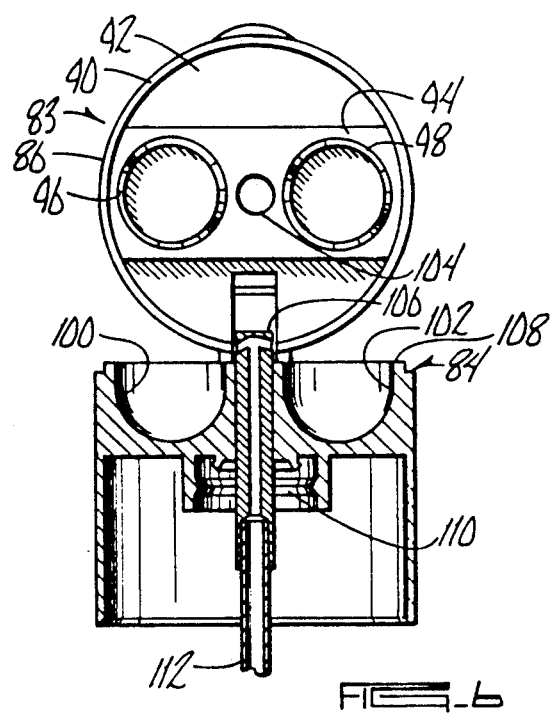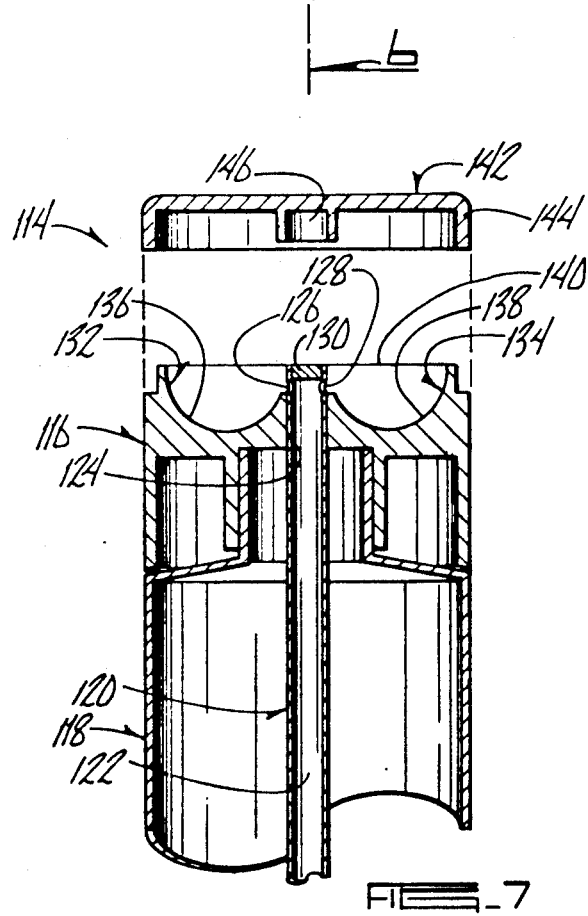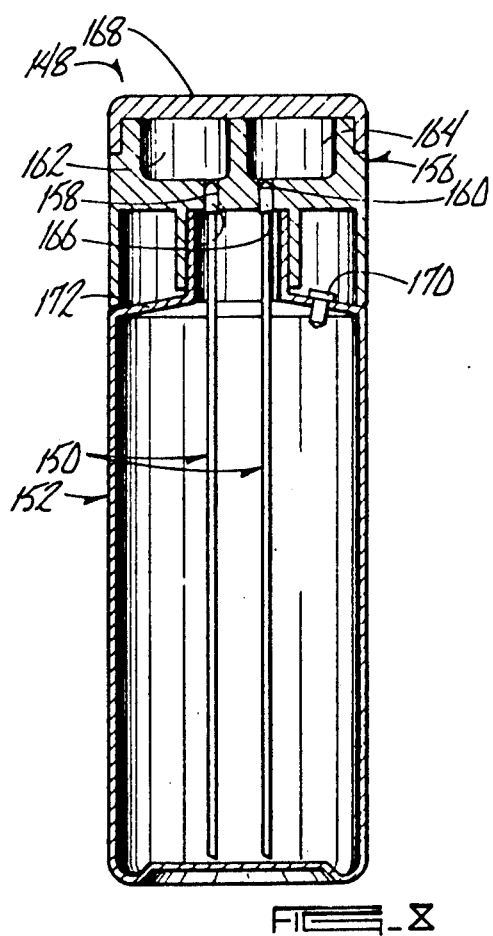

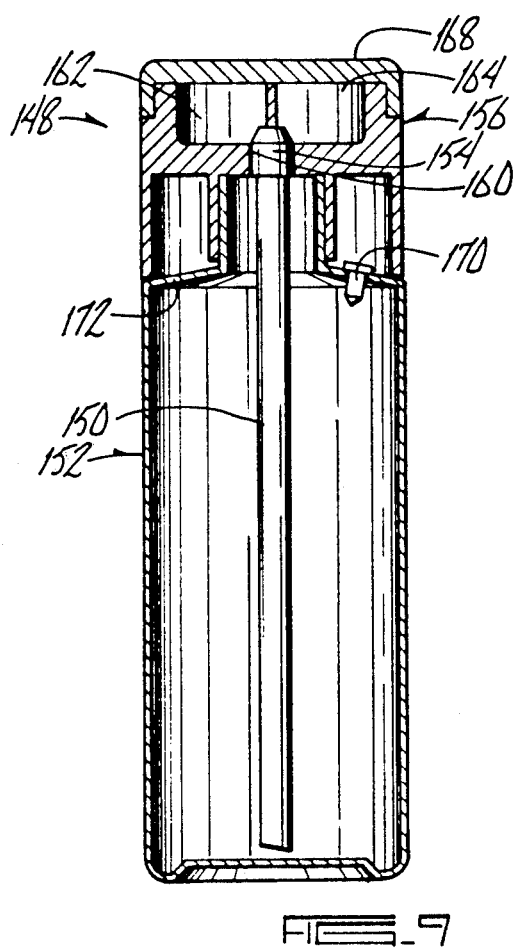
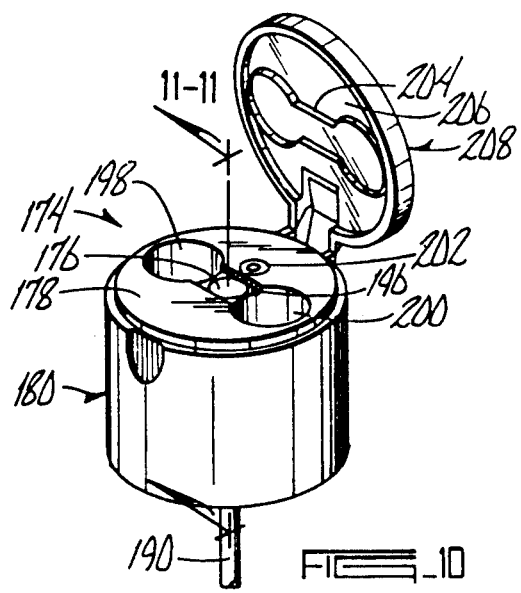
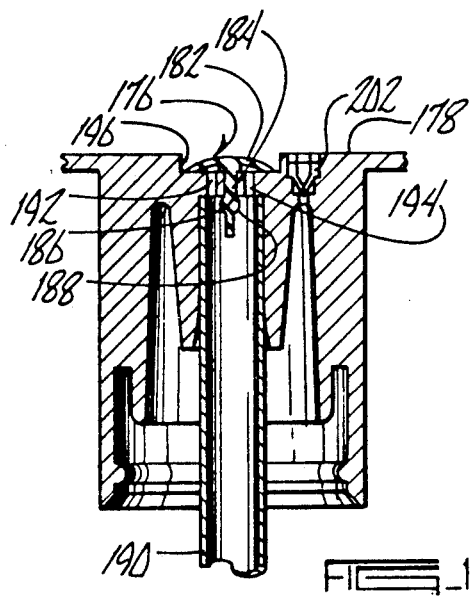
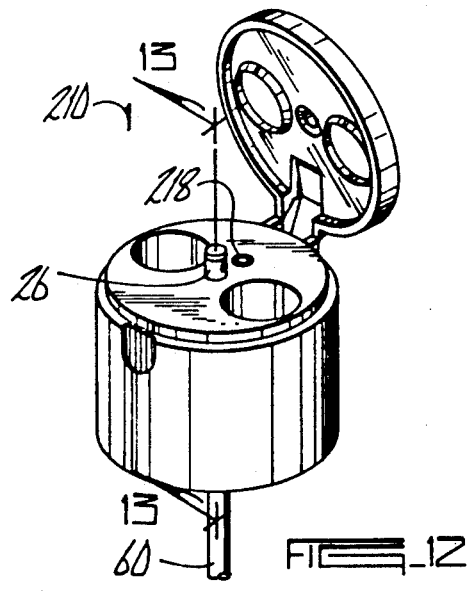
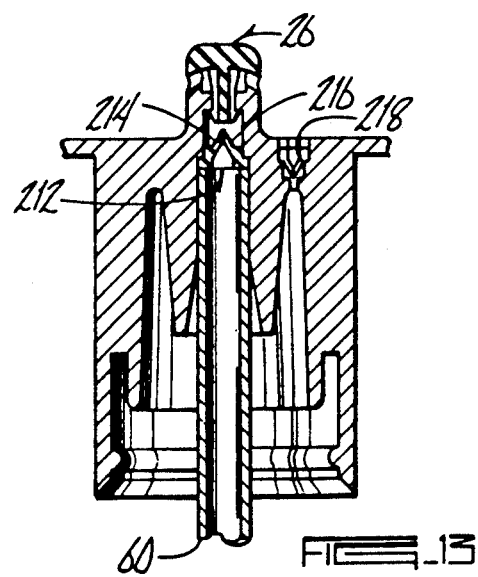

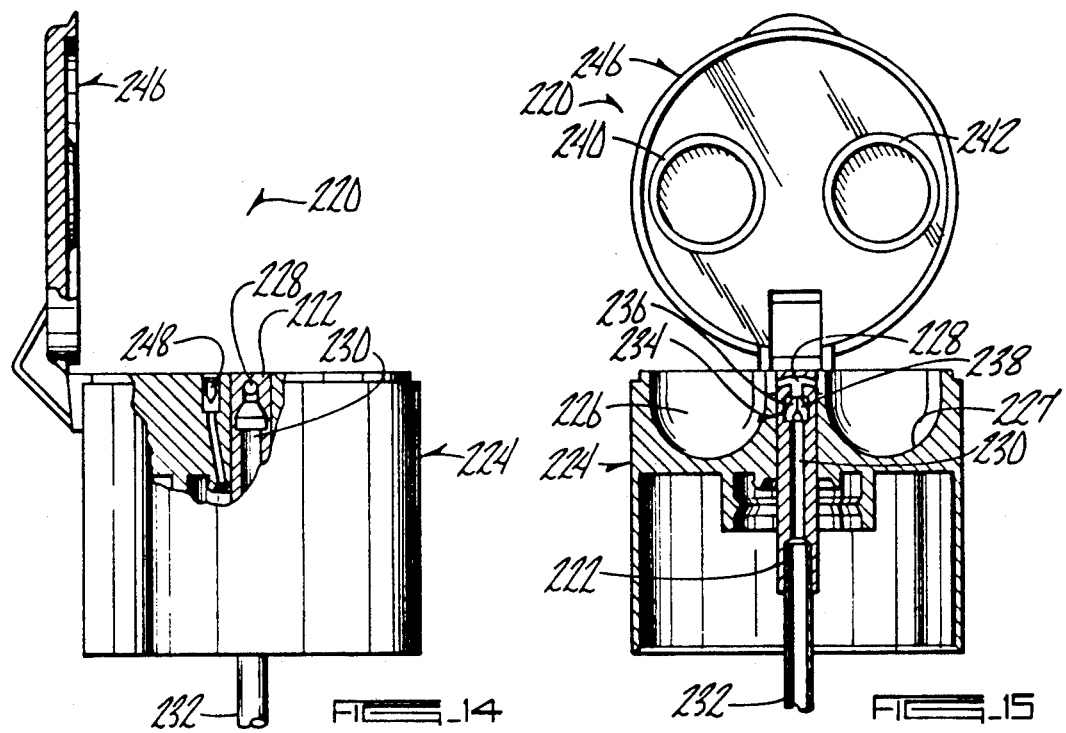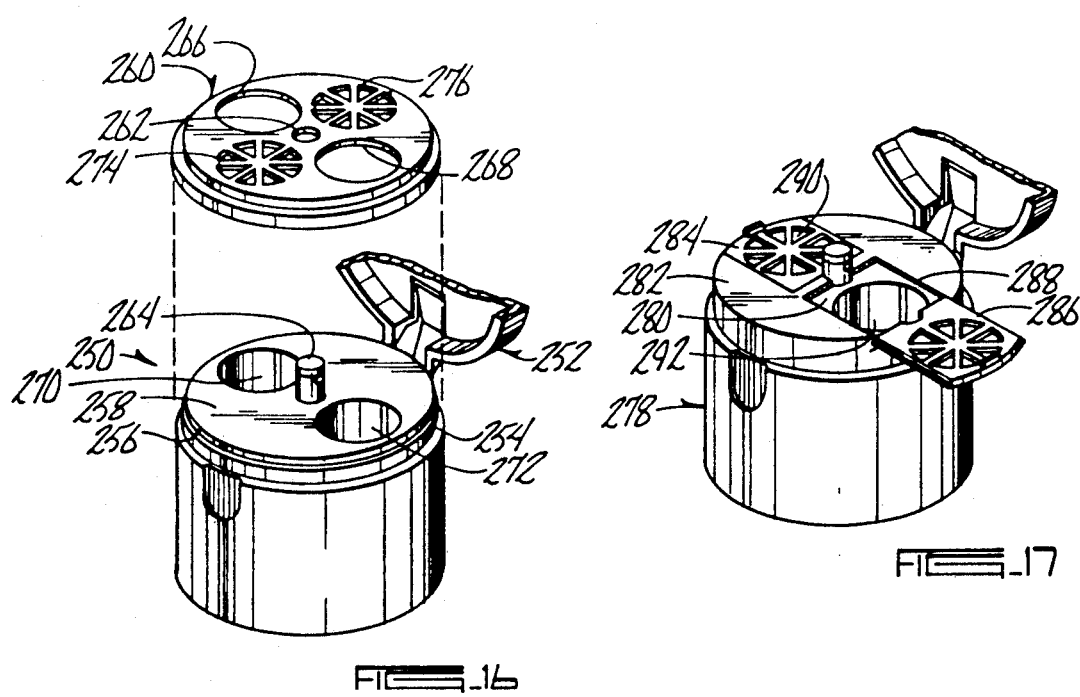

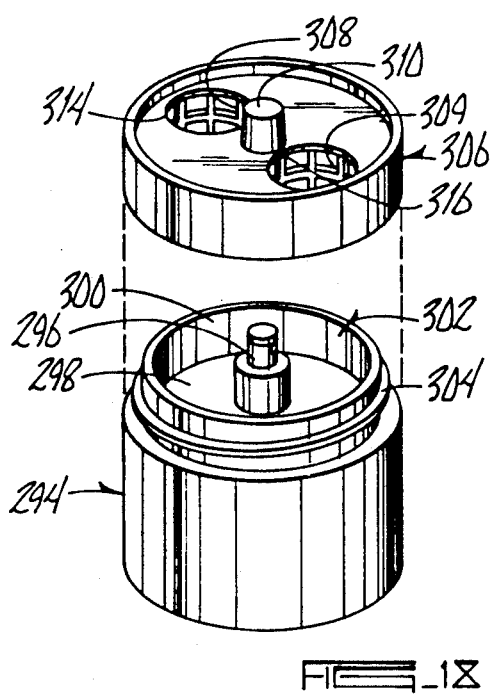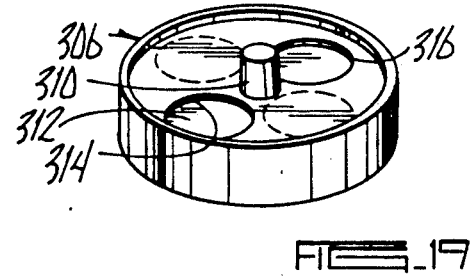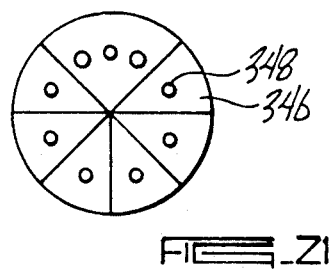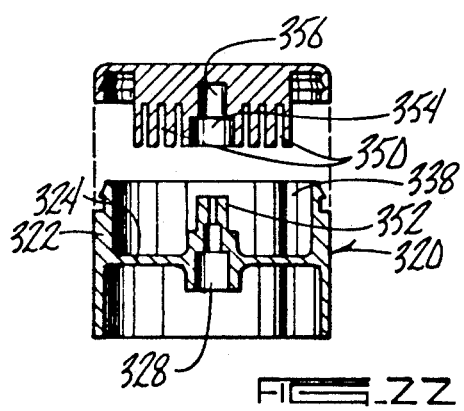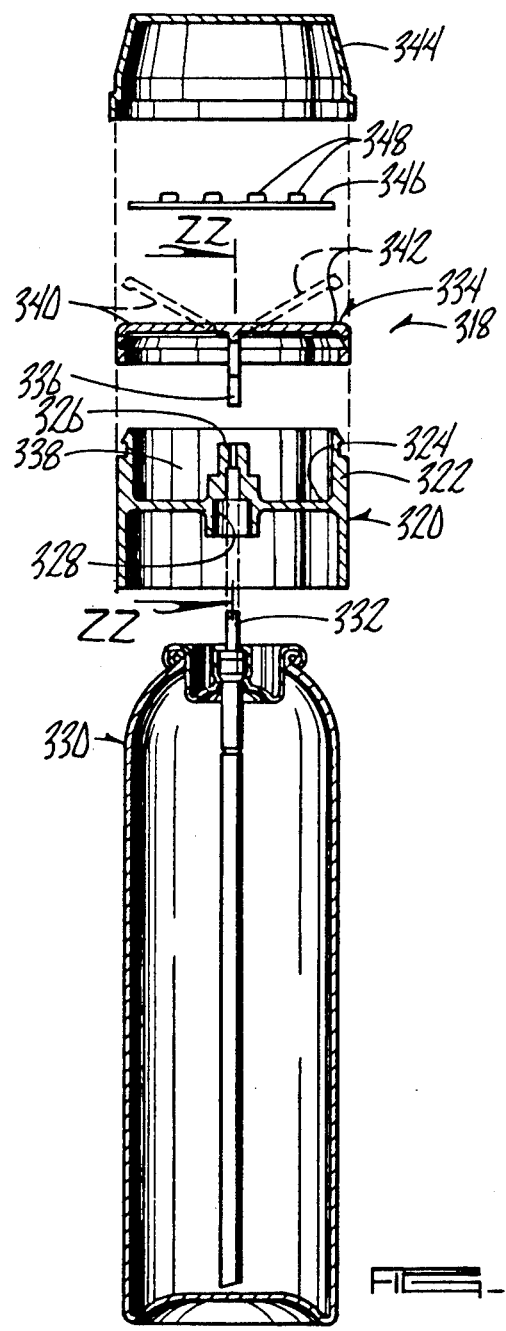

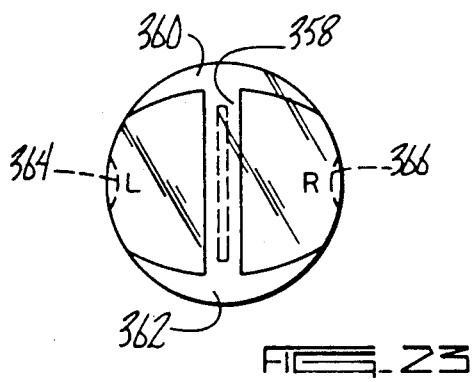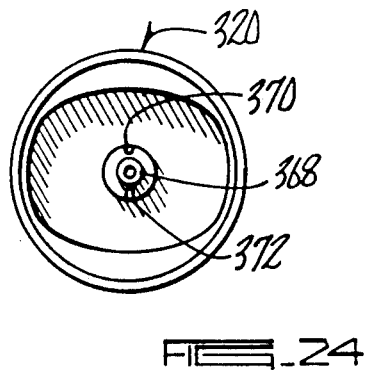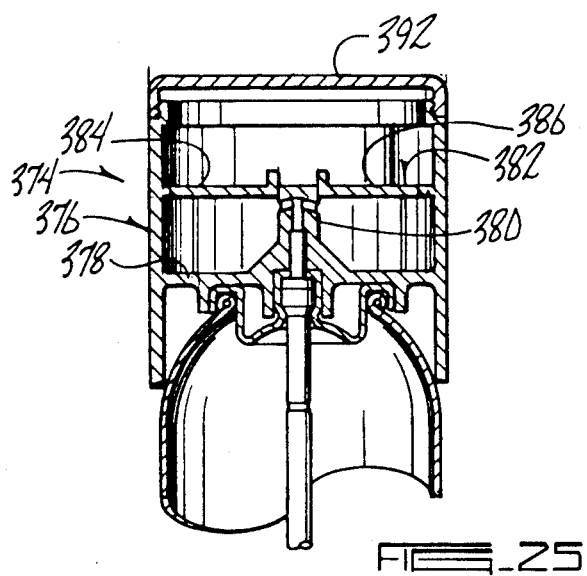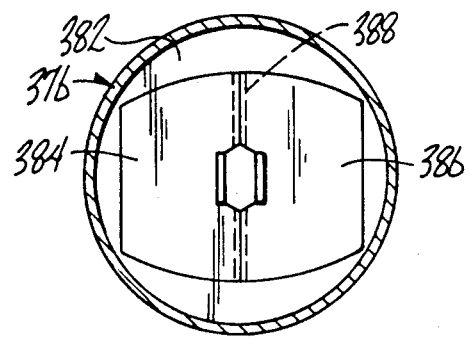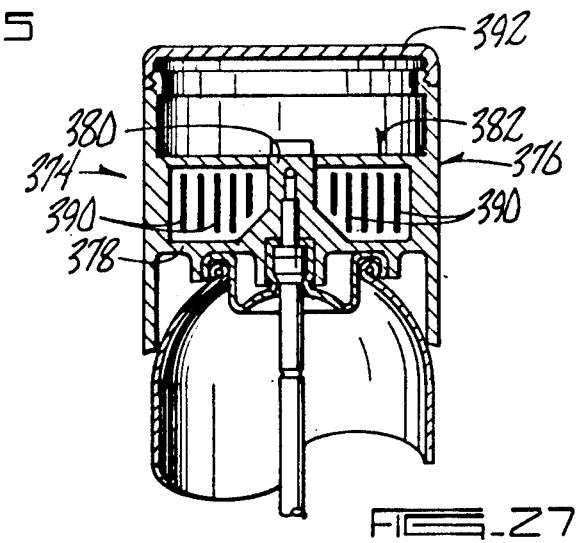

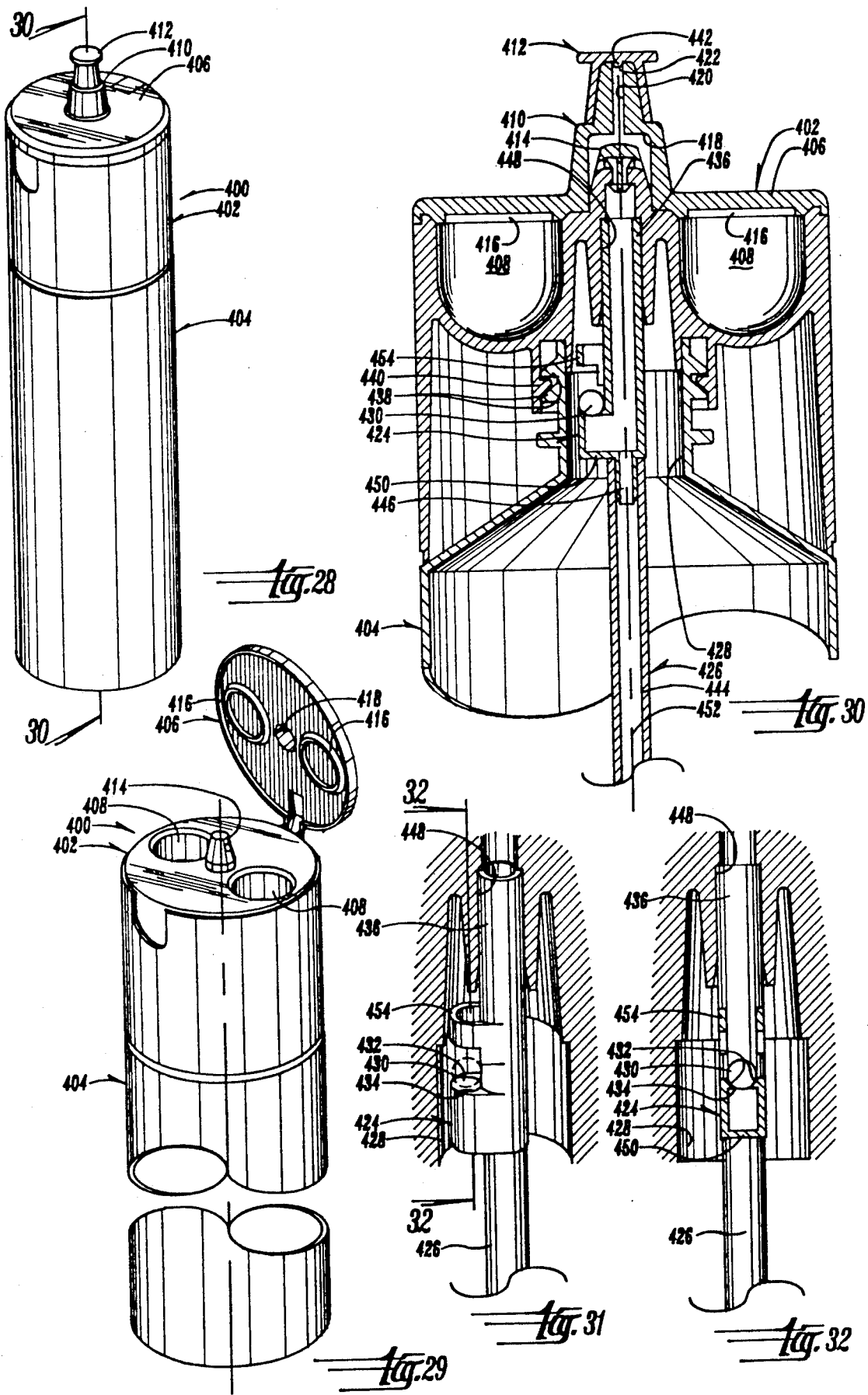

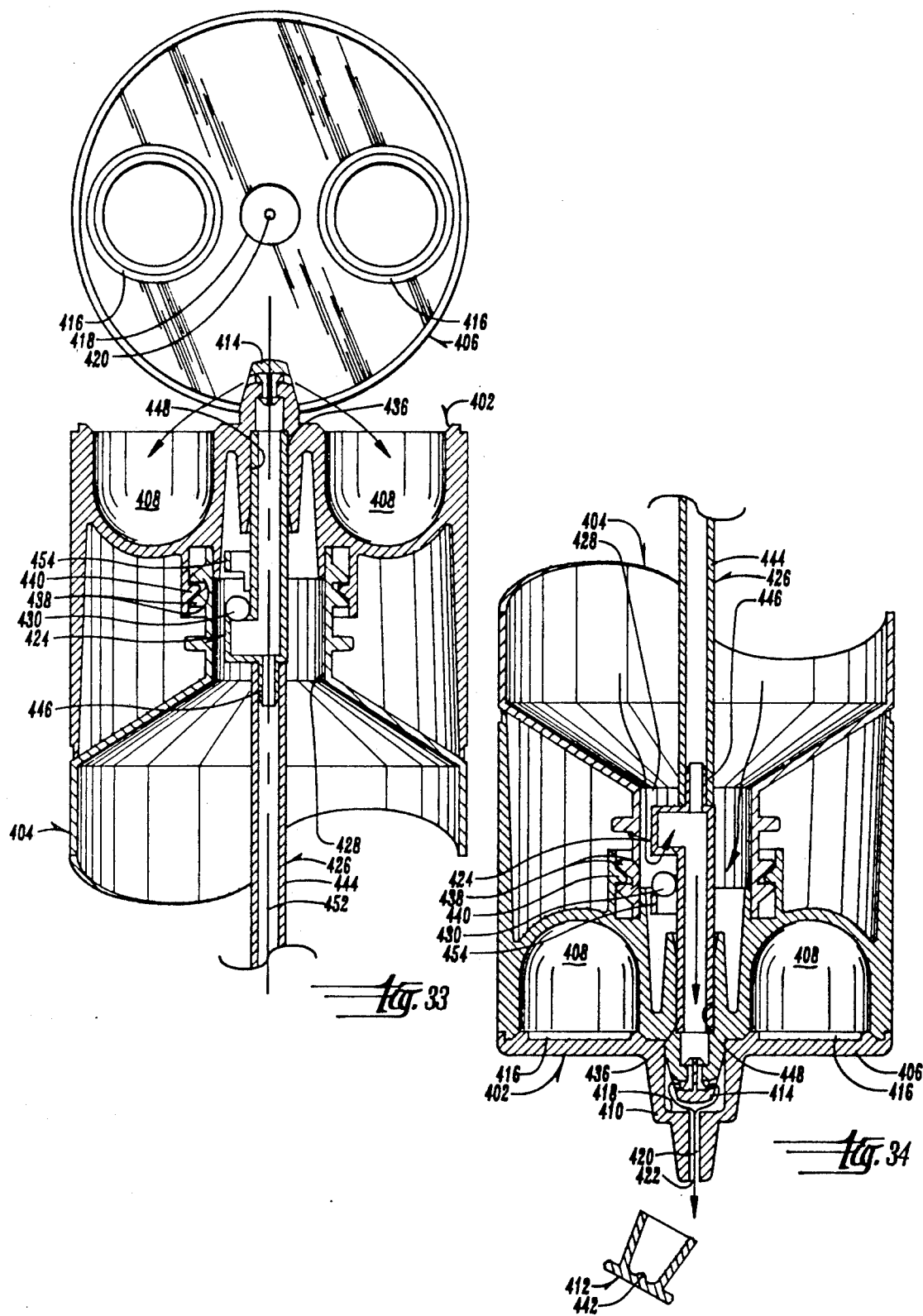

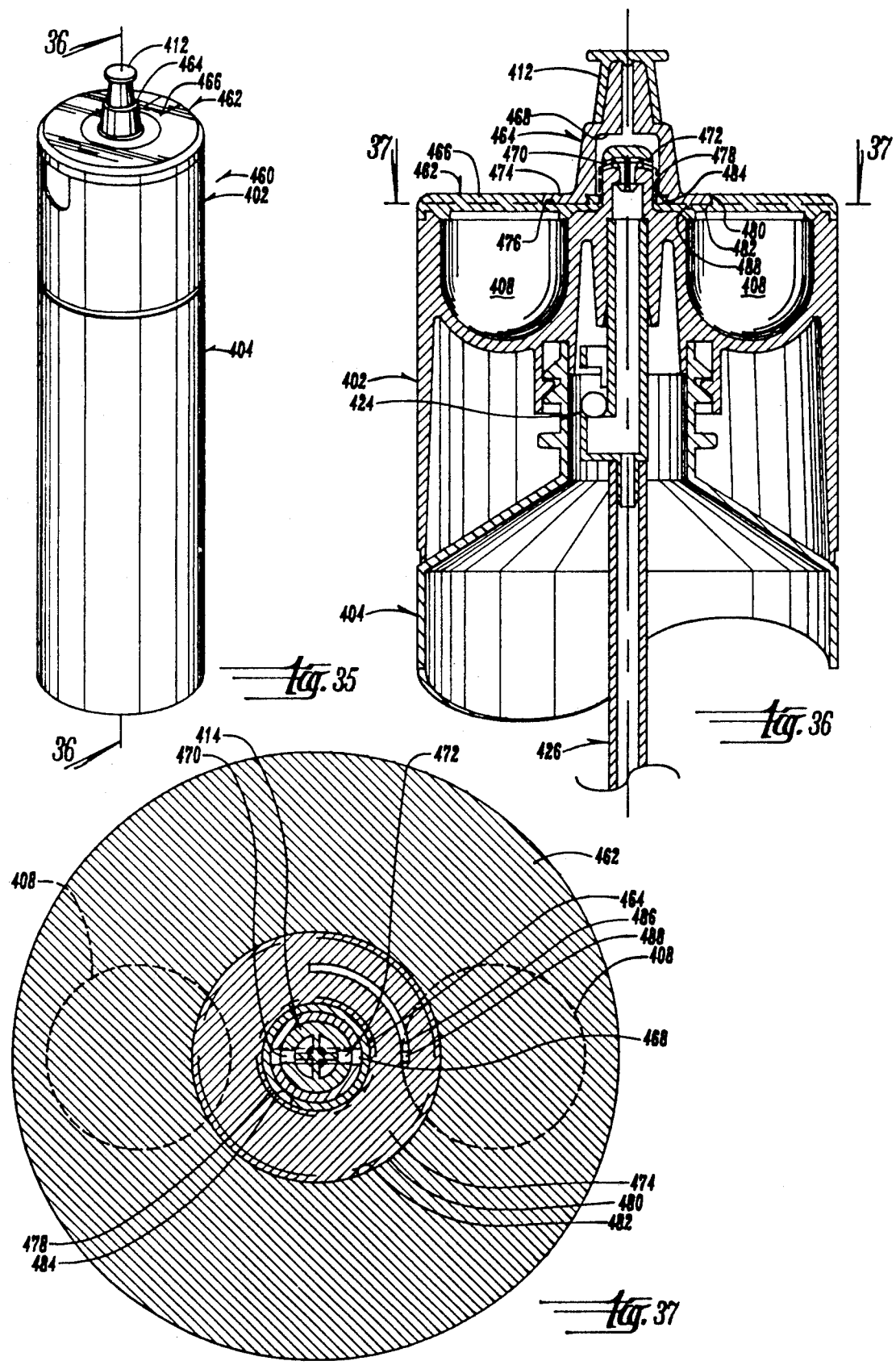

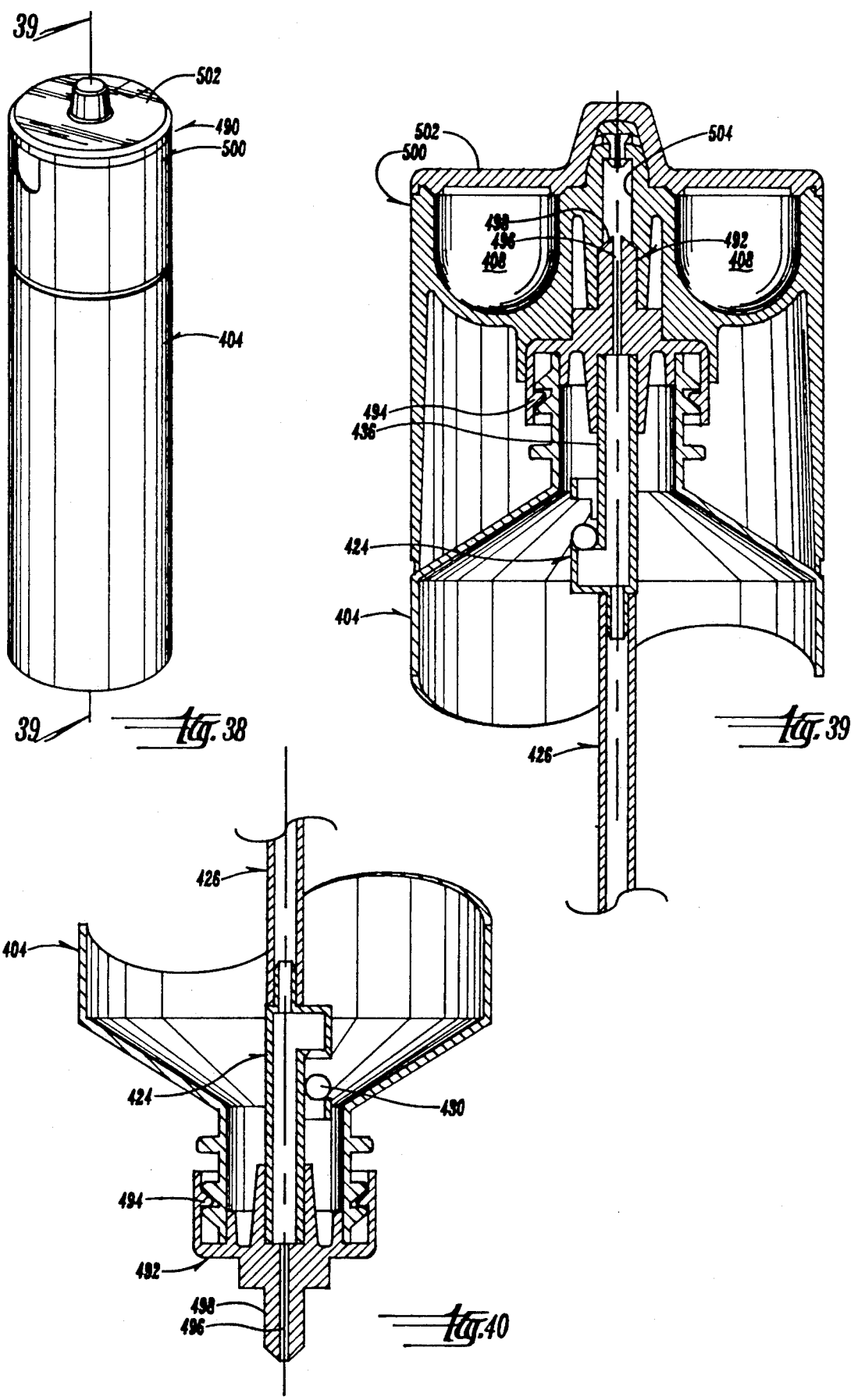

SYSTEM FOR STORAGE AND CARING FOR CONTACT LENSES

This is a continuation-in-part of copending application Ser. No. 07/235,589 filed on Aug. 24, 1988, now U.S. Pat. No. 4,905,819.

BACKGROUND OF THE INVENTION

1. Field of the Invention

The present invention relates to care for contact lenses, and in particular, to cleaning, rinsing, storing, disinfecting, lubricating, dispensing fluid, and the like with respect to contact lenses.

2. Problems in the Art

Contact lenses have proven to be a desirable alternative to eye glasses. However, they require significant and repetitive maintenance and care. Because of the sensitive and fragile nature of the human eye, and the close association of contact lenses to the eye, to maintain comfort and usability, periodic treatment of contact lenses is necessary.

Depending on the nature of the contact lens, the recurring periods for care and maintenance differ, but the functions are similar. For example, all contact lenses must be kept clean from foreign matter to maintain clarity and reduce abrasion to both the contact lens and the user's eye. Some lenses require periodic disinfecting, and others require periodic lubrication. Furthermore, because of the nature of these type of substances, the contact lenses must be thoroughly rinsed and cleaned before being reused.

Some contact lenses require periodic soaking to maintain a level of wetness to allow optimal comfort for a user. Furthermore, when contact lenses are not being used, their fragile and transparent nature require a secure and generally aseptic place for storage. Many times this is in some sort of a soaking, cleaning, or storage fluid.

It furthermore should be understood that because contact lenses, like eye glasses, many times differ in their optical properties from the left to the right eye, it is desirous that any contact lens holder be configured so that the user can easily discern and identify the storage place for the left contact lens in contrast to the right contact lens, especially when the user's vision is generally impaired when contact lenses are out of the user's eyes.

Conventionally, contact lens storage holders are small two-chambered devices, with either screw-on caps, or snap-down caps. To introduce the fluid for the care of the contact lenses, a specified fluid container, such as a squeeze bottle or the like, holding the desired fluid is obtained, and then the contact lens holder is opened up, and the fluid directed into each chamber holding a lens. The caps or lids are then re-covered over the chamber. Any removal of the fluid requires care that the contact lenses not be lost, requires rinsing, and then any refilling with the fluid, or any other fluid, requires the same steps.

Some attempts have been made to combine a contact lens holder with containers carrying some of the needed fluids for care of contact lenses. These attempts have tried to avoid having a contact user carry a separate contact lens holder, with separate contact lens fluid containers. Some of these attempts have simply configured a holder to either be permanently attached, or removably attached to a fluid container. However, it still requires that a contact lens holder or holders be opened up, and the fluid container be opened and oriented to fill the contact lens holder with fluid. This is only a slight improvement over conventional contact lens holders, and in fact, may be more cumbersome. The problem still exists with respect to accuracy in filling the lens holder.

Other attempts have configured a container which is filled with fluid, then the contact lenses are put in some sort of a cage or fluid permeable device, and then inserted into the container. These devices also require multiple steps and handling of a separate fluid bottle to fill the container.

There has also been an attempt whereby a device has an upper chamber and a lower fluid container. The lower fluid container is filled with the desired fluid. The contact lenses are put in some sort of a cage or a fluid permeable frame which is inserted into an upper chamber in the device. Fluid from the lower container is then conveyed to the upper container having the frame holding the contact lens by squeezing or otherwise causing the fluid to be appropriately transported. This again requires special handling of the contact lenses, and numerous steps to achieve its purpose. Such an arrangement is also not generally suitable as a contact lens holder per se.

Therefore, there is a real need to simplify, economize, and make more efficient the means and method for caring for contact lenses. Presently available devices and methods involve fairly complicated structure, require significant handling, and generally utilize separate containers for the lenses and the fluids.

Because contamination is one of the biggest problems with contact lenses, every handling of the lenses, and any part of their containers, including the fluid containers, increases the risk of contamination.

Separate filling of a contact lens holder from an independent fluid container creates accuracy problems. Sufficient fluid is needed in the chamber holding the contact lens to accomplish the function of the fluid, whereas excess creates waste. Also, it is many times cumbersome to handle a separate fluid container, again, especially when the user's contact lenses are out of their eyes.

Another problem involved with contact lens care is the rather consistent need to have fluids used in contact lens care available. Presently, a contact lens user generally has a contact lens holding case and a plurality of bottles of fluid for different purposes, as well as certain chemicals for cleaning or other contact lens treatment. Therefore, a variety of different components are needed to be located and available. While a need has been identified to integrate the contact lens holder and the fluid container with fluid used in the care of contact lenses, it would also be advantageous to have the ability to dispense fluid from the fluid container, not only to the lens holder, but also externally of the combination to an desired location. The user would therefore have the option of a number of functions all within one unit.

It is therefore a primary object of the present invention to provide a means, method and system for storing and caring for contact lenses which overcomes or solves the problems and deficiencies in the art.

A further object of the present invention is to provide a means, method and system as above described which allows storage and caring for contact lenses in a unitary apparatus.

Another object of the present invention is to provide a means, method and system as above described, which allows secure, sealable, and easy placement and storage of contact lenses.

A further object of the present invention is to provide a means, method and system as above described, which provides for easy, economical, and efficient storage of contact lens care fluid and communication of that fluid with the contact lens holder.

Another object of the present invention is to provide a means, method and system as above described which eliminates multiple steps and handling, with regard to storage of the contact lenses, and measuring and pouring of contact lens care fluid.

A further object of the present invention is to provide a means, method and system as above described, which is economical to manufacture, and non-complex in structure, durable, and economical and easy to use.

A further object of the present invention is to provide a means, method and system as above described which enhances accuracy and efficiency of use of lens care fluids.

Another object of the present invention is to provide a means, method and system as above described which promotes an aseptic and non-contamination environment for the storage and handling and care for contact lenses.

A further object of the present invention is to provide a means, method and system as above described which allows selective dispension of fluid used in contact lens care to an external location.

Another object of the present invention is to provide a means, method and system as above described which provides multifunction capabilities all with the promotion of aseptic and noncontaminated environment for storage, handling, care, and dispensing of fluid for contact lenses.

These and other objects, features, and advantages of the invention will be made clearer with reference to the accompanying specification and claims.

SUMMARY OF THE INVENTION

The present invention includes a means, method and system for storing and caring for contact lenses, including, but not limited to, cleaning, rinsing, storing, disinfecting, and lubricating contact lenses while in a holder. The invention allows easy and accurate placement and storage of contact lenses in a holder, while at the same time provides easy and accurate filling of the holder with a desired fluid used in the care of contact lenses. Additionally, the invention can give the user the option of dispensing fluid directly to an external location.

The first aspect of the invention involves a contact lens holder having a chamber for supporting and containing each contact lens. A cap or other cover can be adjustably positioned to enclose each chamber. A fluid conduit means is associated with the holder and provides a pathway for fluid to each chamber. The holder and conduit then include apparatus to communicate with a fluid container holding a desired lens care fluid. The container can either be unitary with the holder, or can be removable or interchangeable with other fluid containers. The contact lenses can thus be securely stored, or fluid from the fluid container can be accurately dispensed into the holder.

In another aspect of the invention, the fluid conduit can include a distributor means for directing fluid to multiple chambers in the contact lens holder. The fluid conduit can also either consist of a direct pathway between the fluid container and the holder, or can contain one way valves allowing fluid to pass from the container to the holder, but disallowing the passage of fluid from the holder back to the container.

A further aspect of the invention involves structure which can be adjustably positioned with respect to the chambers holding the contact lenses in the contact lens holder providing screens, strainers, or cages to retain the lenses in the chambers, yet allow fluid or pressurized fluid to pass therethrough for rinsing or other purposes. The apparatus can be adjusted between presenting a screen, grate, or cage with respect to the contact lenses, to simply allowing an opening to the chambers for easy access to the contact lenses.

A further aspect of the invention involves the manner in which fluid from the fluid container is conducted to the holder. In one embodiment, the fluid container consists of a squeezable bottle wherein squeezing causes the movement of fluid through an outlet from the bottle through the fluid conduit to the holder. A second embodiment utilizes an aerosol container whereby movement of the lens holder with respect to the fluid container causes expulsion of fluid from the aerosol fluid container into the holder.

A still further aspect of the invention involves an optional attachment to the holder for storing other contact lens care items such as tablet form chemicals, which can be introduced into the contact lens holder with fluid for contact lens care purposes. The invention, in its many aspects, therefore, presents a means, method and system for storing and caring for contact lenses which provides ease of use, accuracy, security, and efficiency for contact lens users. It also provides an economical and efficient system to manufacture, package, and market.

Another aspect of the invention gives the user the option of what has been described above; namely selection between simply storing of contact lenses, treating contact lenses by providing fluids to the storage container, and having those options available in one integrated unit. Additionally, an aspect of the invention includes presenting the option of being able to dispense the fluid used in the care of contact lenses to an external location. This too would be integrated into one unit to further enhance the flexibility of the invention.

BRIEF DESCRIPTION OF THE DRAWINGS

FIG. 1 is a perspective view of one embodiment of the invention, showing a contact lens holder lid in an open position.

FIG. 2 is a partial perspective view with a cut-away portion of the embodiment of FIG. 1, showing the holder lid in a closed position.

FIG. 3 is an elevational cross-sectional view of the embodiment of FIG. 1 with the holder lid in a closed position.

FIG. 4 is an enlarged elevational sectional view of a portion of FIG. 3.

FIG. 5 is an elevational view of the contact lens holder portion of an alternative embodiment of the invention, with the holder cap shown in cross-section and in an open position.

FIG. 6 is a sectional view taken along lines 6—6 of FIG. 5.

FIG. 7 is an elevational cross-sectional view of a still further embodiment of the invention, showing a removable cap for the contact lens holder in a removed position.

FIG. 8 is an elevational cross-sectional view of another embodiment of the invention, including a one way valve between the fluid holding container and the contact lens holder.

FIG. 9 is a side elevational cross-sectional view of the embodiment of FIG. 8.

FIG. 10 is a perspective view of a contact lens holder for an additional embodiment of the invention showing the lid for the holder in an open position.

FIG. 11 is a side elevational cross-sectional view taken along lines 11—11 of FIG. 10.

FIG. 12 is a perspective view of the contact lens holder of a further embodiment of the present invention with the holder lid in an open position.

FIG. 13 is a side elevational cross-sectional elevational view shown along lines 13—13 of FIG. 12.

FIG. 14 is a side elevational view of another embodiment of the contact lens holder of the present invention, with the holder lid shown in cross-section and in an upright position, and with a cut-away portion showing a return air valve.

FIG. 15 is a front elevational cross-sectional view taken along lines 15—15 of FIG. 14.

FIG. 16 is a perspective view of another embodiment of the invention showing a contact lens holder with a lid partially shown in an open position, and a removable rotatable adjustment member which can be positioned over the contact lens holding chambers.

FIG. 17 is a perspective view of another embodiment of the contact lens holder of the present invention similar to that of FIG. 16, showing adjustable strainers which can be positioned over the contact lens holding chambers.

FIG. 18 is a still further embodiment of the present invention showing a contact lens holder, with a removable head portion which includes cages for holding the contact lens.

FIG. 19 is a perspective view of the head portion of the embodiment of FIG. 18 showing that a portion can be adjusted to close off the openings into the cages for holding the contact lenses.

FIG. 20 is a front elevational cross-sectional exploded view of a further embodiment of the present invention including an aerosol fluid container, a contact lens holder having a cap with hingeable lids to each contact lens chamber, and an overcap for releasably holding contact lens care chemical tablets to the contact lens holder.

FIG. 21 is a top plan view of a tablet sheet for the embodiment of FIG. 20.

FIG. 22 is a side elevational cross-sectional view of the cap and the distributor head for the lens holder of the embodiment of FIG. 20.

FIG. 23 is a top plan view of the cap for the lens holder of the embodiment of FIG. 20.

FIG. 24 is a top plan view of the lens holder of the embodiment of FIG. 20.

FIG. 25 is a partial elevational cross-sectional view of a further embodiment of the invention similar to that of the embodiment of FIG. 20.

FIG. 26 is a top plan view of the cap for the embodiment of FIG. 25, having hinged lids for access to the chambers holding contact lenses.

FIG. 27 is a partial side elevational cross-sectional view of the interior of the lens holder for the embodiment of FIG. 25.

FIG. 28 is a perspective view of a still further optional embodiment of the present invention incorporating the options of contact lens storage in a contact lens holder attached to a fluid container, with the added feature of a dispensing tip to dispense fluid from the fluid container externally of the device.

FIG. 29 is a partial perspective view of the embodiment of FIG. 28 showing the cover to the contact lens holder in an open position, as opposed to the closed position of FIG. 28.

FIG. 30 is a sectional view taken along lines 30—30 of FIG. 28.

FIG. 31 is an interior perspective view of a 360° valve used in the embodiment of FIG. 28.

FIG. 32 is a sectional view taken along lines 32—32 of FIG. 31.

FIG. 33 is a partial sectional view similar to FIG. 30 with the cover to the contact lens holder in an open position such as is shown in FIG. 29, and showing the fluid flow from the fluid container to the contact lens holder chambers.

FIG. 34 is a sectional view similar to FIG. 30 showing the embodiment inverted to allow dispensing of fluid from the dispensing tip.

FIG. 35 is another embodiment similar to that of FIG. 28 shown in perspective.

FIG. 36 is a partial sectional view taken along lines 36—36 of the embodiment of FIG. 35.

FIG. 37 is a sectional view taken along lines 37—37 of FIG. 36.

FIG. 38 is another embodiment similar to those shown in FIGS. 28 and 35.

FIG. 39 is a partial sectional view taken along lines 39—39 of FIG. 38.

FIG. 40 is a partial sectional view of the embodiment of FIGS. 38 and 39 but inverted and with the contact lens holder portion removed to expose an interior dispensing tip for dispensing of fluid from the fluid container to an external location.

DETAILED DESCRIPTION OF THE PREFERRED EMBODIMENT

With reference to the drawings, a detailed description of the preferred embodiments of the invention will follow. Reference numerals will be utilized to identify certain features and parts of the embodiments. Like reference numerals will be used to identify like parts in the drawings.

The drawings and these detailed descriptions are intended to give the reader an understanding of some of the different forms the invention might take, and some of the different features the invention might include. These examples are not intended to and do not limit the scope of the invention.

With particular reference to FIG. 1, first embodiment 10 of the invention is shown in perspective. A contact lens holder 12 includes an annular side wall 14 and a top wall 16. Recessed chambers 18 and 20 are defined by cupped walls 22 and 24 extending downwardly from top wall 16 and interiorly of annular side wall 14. Chambers 18 and 20 receive left and right contact lenses, support them, and also can receive fluids for storage, cleaning, rinsing, disinfecting, lubricating, and other functions with respect to contact lenses.

A distributor head 26 of fluid conduit 28 (see also FIGS. 2–4), extends upwardly from or through top wall 16 and includes orifices 30 and 32 on opposite lateral sides which are directed towards chambers 18 and 20, respectively. The fluid through fluid conduit 28 and distributor head 26 thus is directed by orifices 30 and 32 into chambers 18 and 20 when desired.

Lens holder 12 is positioned on top of a fluid container 34, which holds fluid for lens care. Fluid conduit 28 is in fluid communication with the interior of fluid container 34. It is to be understood that fluid container 34 could be integrally formed with lens holder 12, but is preferred that fluid container 34 be removably securable to lens holder 12 and fluid conduit 28 so that replacement of fluid container 34 or interchangeability of containers holding different lens care fluids can be easily accomplished.

A lid or cap 36 is hingeably connected to lens holder 12 by hinge 38. Bottom side 40 of cap 36 contains two downwardly extending rings 42 and 44 which are positioned so as to matably fit within the recessed chambers 18 and 20 in lens holder 12. Ideally, rings 42 and 44 would fixedly fit therein and seal any fluid inlet or outlet to chambers 18 and 20.

Top side 46 of cap 36 includes an extended portion 48 which covers aperture 50 in the center of cap 36. The cavity 52 extends up into extended portion 48 from aperture 50, to allow distributor head 26 to be inserted therein when cap 36 is moved from its open position shown in FIG. 1, to a closed position (shown in FIG. 2). It is to be understood that aperture 50 and cavity 52 could be configured so as to sealingly fit over distributor head 26 to deter any fluid passage from distributor head 26. Lens holder 12 can also have a raised edge 54 to cooperate with annular flange 56 of cap 36 to cause a secure fit between cap 36 and lens holder 12 when in a closed position. A notch 58 in the side wall 14 of lens holder 12 would permit access to annular flange 56 of cap 36 to raise it from the closed position shown in FIG. 2. This configuration would allow embodiment 10 to have a smooth annular side wall from cap 36 down through lens holder 12 and fluid container 34.

FIG. 2 not only shows cap 36 in a closed position, but also shows tube 60 of fluid conduit 28. Tube 60 would form a fluid passageway between fluid container 34 and distributor head 26 and could either be permanently secured to lens holder 12, or be removable. If removable, if tube 60 and fluid container 34 were removable from lens holder 12, lens holder 12 with cap 36 could function independently as a contact lens holding case.

FIG. 3 shows in elevational cross-section, the general configuration of the interior of lens holder 12, including cap 36, fluid conduit 28, and fluid container 34. Cap 36 is shown in the closed position covering cupped walls 22 and 24 defining chambers 18 and 20 for holding left and right contact lenses.

Walls 22 and 24 are cupped to provide easy insertion and removal of the small fragile contact lenses, and also to allow thorough cleaning of chambers 18 and 20, by eliminating any corners. FIG. 3 shows that fluid container 34 has a basically tubular body 62 topped by upwardly angled shoulder 64, and neck 66. The exterior of neck 66 includes threads 68 which matably engage threaded socket 69 extending downwardly from the outside of cupped walls 20 and 22 of lens holder 12.

Fluid container 34 thus can be threaded into socket 69 until the bottom of annular side wall 14 of lens holder 12 abuts shoulder 64 of fluid container 34. Lens holder 12 and fluid container 34 would then be firmly secured together in a sealing relationship.

Fluid conduit 28 includes tube 60 extending from near the bottom of the interior of fluid container 34 up through neck 66 of fluid container 34, and socket 69 of lens holder 12 into a bore 70 in lens holder 12. Bore 70 has a wider lower end 72 which receives tube 60, but then narrows to frictionally grasp and secure tube 60 therein. Bore 70 also extends to distributor head 26 to allow a complete fluid passage from fluid container 34 to distributor 26.

As can be seen in FIG. 3, when lid 36 is in a closed position, fluid cannot travel from fluid container 34 out of distributor head 26, or into chambers 18 and 20. Furthermore, fluid cannot pass out of chambers 18 and 20.

FIG. 4 shows in enlarged detail that distributor head 26 has an enlarged head 74 and a downward extending portion 76, so that distributor head 26 is generally T-shaped in cross-section. Portion 76 has at its lower end a smaller head 78 which cooperates with interior annular flange 80 of lens holder 12 to allow distributor head 26 to be snapped-in to position. Orifices 30 and 32 exist on opposite sides of divider wall 82 of downwardly extending portion 76. Divider wall 82 serves to direct fluid traveling up tube 60 and bore 70 equally into orifices 30 and 32. It is to be further understood that orifices 30 and 32 are in a raised position above top wall 16 of lens holder 12, but in a somewhat downwardly angled orientation so that fluid under pressure will be directed in a stream or focus spray into recess chambers 18 and 20. Orifices 30 and 32 are configured so as to form an easily controlled directional stream to each recessed chamber 18 and 20 to enhance accuracy and avoid waste. Furthermore, fluid conduit 28 is configured so that by squeezing the flexible and resilient body 62 of fluid container 34, pressure will cause fluid to travel up tube 60 into distributor head 26 for easy and controllable filling of chambers 18 and 20, and easy and controllable stoppage of filling by releasing pressure on tubular body 62.

FIGS. 5 and 6 depict a lens holder 84 which is slightly different from lens holder 12 of embodiment 10, but operates upon the same principles. Lens holder 84 differs only in that instead of having an extended portion raising from the middle of the cap, to produce a protrusion, cap 86 of lens holder 84 has a flat top surface 88. The annular side wall 90 of cap 86 is taller than annular flange 56 of cap 36 of embodiment 10. Bottom side 92 of cap 86 of lens holder 84 has a solid portion 94 which includes springs 96 and 98 for sealing off cupped chambers 100 and 102 in lens holder 84. Solid portion 94 also includes a straight serrated bore 104 which would cover and contain distributor head 106.

It can also be seen that distributor head 106 stands from outside and above top wall 108 of lens holder 84, all the way down through threaded socket 110. It then receives tube 112. This arrangement differs slightly from that of embodiment 10 shown specifically in FIGS. 3 and 4, but operates essentially the same. FIG. 7 shows a still further embodiment 114 of the invention, similar to embodiments 10 and 83 previously described. Embodiment 114 utilizes a lens holder 116 and a fluid container 118 which function as described with respect to previous embodiments. However, in embodiment 114, fluid conduit 120 is comprised solely of tube 122 which extends from fluid container 118 through bore 124 in lens holder 116. Tube 122 has small orifices 126 and 128 near its top end, and a plug 130 above orifices 126 and 128 in its top end. Cup chambers 132 and 134 have adjacent inner side walls 136 and 138 which are lowered in the position of orifices 126 and 128 so that cup chambers 132 and 134 can be in direct fluid communication with orifices 126 and 128 and tube 122. Thus, there is no distributor head which extends above top wall 140 of lens holder 116. Orifices 126 and 128 are positioned so that fluid can fill in cup chambers 132 and 134 to a level to cover contact lenses positioned therein, but fluid will not drain out back into the tube 122 unless filled up to orifices 126 and 128.

Cap 142 thus simply fits around annular wall 144 of lens holder 116, and contains a sleeve 146 which surrounds orifices 126 and 128 and tube 122 when positioned upon lens holder 126, this serves to seal off any fluid communication between chambers 132 and 134, and orifice 126 and 128.

FIGS. 8 and 9 depict embodiment 148 which functions similarly to embodiments 10, 83 and 114 except as follows.

Tube 150 extends from the bottom of fluid container 152 to a one way valve assembly 154 positioned in lens holder 156 (see particularly FIG. 9). As schematically shown in FIG. 8, one way valve assembly 154 consists of parallel channels 158 and 160 which extend from tube 150 into cupped chambers 162 and 164, respectively. Each channel contains a one way valve 166 such as are known in the art. In the embodiment of FIG. 8, valves 166 are called "duck-bill" valves as they open when fluid under pressure from tube 150 forces against them to allow fluid into chambers 162 and 164, but close when fluid under pressure through tube 150 is relaxed.

Cap 168 removably is securable over cup chambers 162 and 164 to allow access thereto. Fluid container 152 can either be secured to lens holder 156, or be detachable, such as previously described. Tube 150 could either form a part of lens holder 156 or fluid container 152, or could be detachable from either.

In order to enhance operation of the embodiment of FIGS. 8 and 9, an air valve 170 is positioned through an aperture in shoulder 172 of fluid container 152. Air valve 170 functions as is known in the art, similarly to a one-way valve, by sealing off fluid container 152, except after it is squeezed, when valve 170 operates to allow a supply of air into the interior of fluid container 152, but disallowing any fluid to escape therethrough. Thus, squeezing of fluid container 152 operates to build up pressure in container 152 to force fluid up tube 150, but upon release of fluid container 152, air valve 170 allows equalization of pressure in fluid container 152, and allows it to return to its original state.

FIGS. 10-15 show alternative embodiments for a lens holder utilizing a valve in the fluid conduit. In FIGS. 10 and 11, there is shown embodiment 174 wherein a one way valve 176, called an "umbrella valve" is positioned in top wall 178 of lens holder 180. As can be seen most clearly in FIG. 11, umbrella valve 176 is comprised of a head portion 182 attached to a stem portion 184 which slidably is positioned in bore 186 through top wall 178. A biasing member 188 holds umbrella valve 176 in the position shown in FIG. 11. However, when fluid under pressure flows up tube 190, according to the manner previously described with other embodiments, the fluid will pass through parallel bores 192 and 194 which communicate with tube 190 and cause head portion 182 of umbrella valve 176 to move upwardly. The fluid would then flow in duct 196 to both chambers 198 and 200 holding the lenses. Upon release of pressure up through tube 190, biasing member 188 would force umbrella valve 176 back to a covering relation over bores 192 and 194.

FIGS. 10 and 11 also show a one way duck bill valve 202 which functions as an air valve similar to that described with respect to embodiment 148 in FIGS. 8 and 9. FIG. 10 further shows that a flange 204 can be positioned on the bottom side 206 of cap 208 of embodiment 174 and be of such a configuration that it follows the enclosed shape defined by duct 196, and portions of the perimeter of chambers 198 and 200, so that if desired, the fluid can flow between chambers 198 and 200, or one way valve 176 can operate even if cap 208 is in closed position. On the other hand, it can be configured so that when cap 208 is in a closed position, it does not permit one way umbrella valve 176 from opening. This can be designed according to choice.

FIGS. 12 and 13 show embodiment 210 which is essentially the same as embodiment 10 shown in FIGS. 1-4 except that a duck bill one-way valve 212 is positioned on tube 60 and distributor head 26 in bore 70. Again, when fluid under pressure travels up tube 60, opposite sides 214 and 216 open to allow passage of the fluid to distributor head 26. When pressure decreases to less than the closing biasing force of sides 214 and 216, sides 214 and 216 close off any fluid communication through valve 212 in either direction. Additionally, FIG. 13 shows duck bill one way valve 218 utilized as an air vent for embodiment 210.

Embodiment 220 of FIGS. 14 and 15 is depicted to show an alternative embodiment for the invention whereby a distributor head 222 is positioned in lens holder 24 between chambers 226 and 228, similarly to the embodiment depicted by reference numeral 114 in FIG. 7. Distributor head 222 includes a T-shaped passage 228 which communicates with passage 230, which in turn communicates with tube 232. A duck bill one way valve 234 is positioned in passage 230 directly before T-shaped passage 228 in a manner in which halves or sides 236 and 238 open when fluid pressure of a sufficient force is exerted through tube 232 to distribute fluid through T-shaped passage 228 into chambers 226 and 227.

Two ring flanges 240 and 242 on the bottom side of cap 246 could seal off chambers 226 and 227 when cap 246 is in a closed position. One way valve 234 would eliminate the need for any other structure in cap 246 to seal off T-shaped passage 228.

FIG. 14 also shows that a return air valve 248 could be positioned in lens holder 224 and function as previously described in other embodiments.

FIG. 16 shows another aspect of the invention. A lens holder 250, similar in function to embodiment 10 of FIG. 1, or embodiment 210 of FIG. 12, having a hinged cap 252, could also contain threads 254 along raised vertical edge 256 around the perimeter of top wall 258 of lens holder 250. A rotatable cover member 260, having threads (not shown) matable with threads 254, can optionally be threaded onto threads 254 of lens holder 250. As can be seen, cover member 260 has a center aperture 262 through which distributor head 264 would slidably pass. On opposite sides of aperture 262 are apertures 266 and 268 which are generally the same diameter as chambers 270 and 272 in lens holder 250. By threading cover member 260 upon lens holder 250 to where apertures 266 and 268 are aligned with chambers 270 and 272, access to chambers 270 and 272 is the same as if cover member 260 were not in position on lens holder 250. Thus, contact lenses can be inserted and withdrawn and cap 252 can be closed down to secure lenses therein. Also, lens holder 250 could be operated in association with a fluid container to fill chambers 270 and 272 with lens care fluid.

To assist in draining used fluid from chambers 270 and 272, while at the same time retaining contact lenses in chambers 270 and 272, cover member 260 can be rotated generally 90° so that strainers 274 and 276 would align over chambers 270 and 272. Thus, fluid can be either drained from, or rinsed into chambers 270 and 272 without any danger of contact lenses escaping. To then remove the contact lenses, cover member 260 would again be rotated 90° so that apertures 266 and 268 align with chambers 270 and 272.

FIG. 17 shows a lens holder 278 which functions similarly to lens holder 250 of FIG. 16. Instead of a separate threaded cover member containing strainers, a slot 280 extends across top wall 282 of lens holder 278. Strainer pieces 284 and 286 are slidable in grooves 288 along the sides of slot 280 between either a covering position (shown by strainer piece 284), or an open position (shown by strainer piece 286). Like the embodiment in FIG. 16, contact lenses can be easily inserted or removed from chambers 290 and 292, and strainer pieces 284 and 286 can be easily removed to hold them in chambers 290 and 292, even if fluid is dumped from the chambers, or fluid under pressure is rinsed into the chambers.

FIGS. 18 and 19 show a still further optional embodiment of the lens holder according to the invention. In this embodiment, lens holder base 294 has distributor head 296 extending up through top wall 298. Annular wall 300 extends above top wall 298 and surrounds distributor head 296 to form one large circular chamber 302. Annular wall has threads 304 on its outer vertical side.

A cover member 306, having interior threads (not shown) is threadably matable to threads 304 of annular wall 300. Cover member 306 includes cages 308 which extend downwardly from its bottom surface. It is to be understood that cages 308 basically form a basket wherein contact lenses can be inserted and supported, but that fluid can circulate into and around the interior of cages 308. Cover member 306 is further configured so that by turning dial 310, an underplate 312 turns. Rotation of dial 310 90° would cause underplate 312 to rotate to the position shown in FIG. 19 which would cover openings 314, 316 to cages 308 and thus sealingly secure contact lenses within cages 308 and circular chamber 302. It is to be understood that other configurations for cover member 306 are possible to change it between openings to cages 308, and closing those openings.

It can be seen that in the embodiment of FIGS. 18 and 19, that circular chamber 302 can be filled with fluid, contact lenses can be inserted into cages 308, and then cover member 306 can be operated so that dial 310 is turned to close off openings 314 and 316 by under plate 312. Cover member 306 can then be threaded down onto lens holder 294. Alternatively, it is to be understood that under plate 312 might be operated by turning the perimeter of cover member 306. It is further to be understood that dial 310 might have openings to allow fluid from distributor head 296 to pass into cages 308 and 309, and cover member 306 might have a cap to cover it. Other embodiments and features are possible.

FIG. 20 shows a still further embodiment 318 according to the present invention. It operates on generally the same principles of the previous embodiments, except for the following. Lens holder 320 has an annular body 322 divided by a middle wall 324. A distributor head 326 having a stepped center bore 328 extends through the middle of middle wall 324.

FIG. 20 shows an exploded view of embodiment 318. An aerosol fluid container 330 having a depressible actuator tube 332 is insertable into the lower portion of stepped center bore 328 of distributor head 326. Stepped center bore 328 is configured so that if lens holder 320 is pushed downwardly, actuator tube 332 would also be pushed downwardly and expel fluid from aerosol fluid container 330 through and out the top of step center bore 328. When no pressure is put on lens holder 320, the biasing force of actuator tube 332 upwardly, would stop any expulsion of fluid from aerosol fluid container 330.

As further seen in FIG. 320, a cover cap 334 can be releaseably snapped into place over the top of lens holder 320. A dividing wall 336 would straddle distributor head 326, and divide circular chamber 338 into two chambers, one for each of the left and right contact lenses. Cover cap 334 has two hinged lids 340 and 342 which can be lifted to gain access to the two sides of circular chamber 338.

FIG. 20 also shows an optional feature and aspect of embodiment 318. An over cap 344 can be detachably positioned over cover cap 334. In the enclosed space in the interior of over cap 344, additional contact lens care products, chemicals, or items can be stored for easy and convenient access and use. For example, in embodiment 318, a baseboard 346 containing a plurality of dissolvable tablets 348 can be stored in over cap 344. As can be seen in FIG. 21, baseboard 346 can be circular and divided into various segments with indicia giving a user an indication as to when each tablet 348 should be used during a period of time. For example, numbers can be used for each day of the week to indicate when a certain tablet 348 should be inserted into circular chamber 338 which would then be filled with fluid which would dissolve a tablet so that it could achieve its lens care result.

FIG. 22 shows in cross-section cover cap 334 along lines 22-22 of FIG. 20. It can be seen that dividing wall 336 has slots 350 therein to allow fluid to disperse between both sides of dividing wall 336 and circular chamber 338.

FIG. 22 also shows in isolated cross-section distributor head 326. By comparing it to dividing wall 336 of cover cap 334, it can be seen that upper narrow portion 352 of distributor head 326 extends into wide bore portion 354 in dividing wall 336, but cannot pass into narrow bore portion 356 as it is wider than narrow bore portion 356. Therefore, fluid can pass through stepped center bore 328, distributor head 326 into narrow bore portion 356, and out into circular chamber 338 of lens holder 320.

FIG. 23 shows that in embodiment 318, the top of cover cap 334 would have a central rib 358. Arcuate raised portions 360 and 362 are placed at opposite ends of central rib 358. Hinged lids 340 and 342 would then hinge at their intersection with central rib 358, and have their sides defined by arcuate raised portions 360. Notches 364 and 366 on the underside of hinged lids 340 and 342 could be formed on their outer edge to allow grasping to open lids 340 and 342.

FIG. 24 shows a top plan view of lens holder 320. It can be seen that the top edge 368 of distributor head 326 has two opposed notches 370 and 372 which would receive dividing wall 336 of cover cap 334, and hold it in non-rotatable position. Thus, it can be understood that embodiment 318 of FIGS. 20-24 would function as follows. Over cap 344 would be removed along with baseboard 346 holding tablets 348. Hinged lids 340 and 342 would be lifted sequentially and contact lenses would be inserted into the respective left and right sides defined by dividing wall 336 into circular chamber 338. If desired, an appropriate tablet 348 would be removed from baseboard 346 (which could be a blister pack or other well known tablet packaging means) and inserted into any part of circular chamber 338 through hinged lids 340 or 342.

Hinged lids 340 and 342 would then be secured down, and lens holder 320 would be pressed downwardly against aerosol fluid container 330. Fluid would then be conducted from aerosol fluid container 330 through distributor head 326 into circular chamber 338. Slots 350 would allow equal distribution of the fluid, and the fluid would act upon any tablet 348 to dissolve the same. Movement of the fluid would also carry the dissolved table 348 to all parts of circular chamber 338. Baseboard 346 and overcap 344 could then be repositioned over cover cap 334 and embodiment 318 could be left for the tablet and fluid to operate on the contact lenses. After an appropriate time, or as desired, overcap 344 and baseboard 346 would again be removed, and contact lenses could be removed and the fluid dumped. Lens holder 320 could then be rinsed and cleaned and be prepared for another use.

It is further to be understood that lens holder 320 of embodiment 318 could also be used separately as a lens holder with or without overcap 344.

FIG. 25 shows embodiment 374, which is similar to embodiment 318 of FIG. 20 except for the following. Lens holder 376 has a lower wall 378 through which extends distributor head 380. An upper wall 382 has hinged lids 384 and 386. Furthermore, divider wall 388 (particularly FIG. 28, functions like that of embodiment 318 as shown in FIGS. 20 and 22), having slits therein to allow transfer of fluid between opposite sides of lens holder 376. A baseboard holding tablets such as shown in FIG. 21 could then be stored in the space between upper wall 382 and screw cap 392 on lens holder 376.

FIG. 26 shows that upper wall 382 is of a configuration similar to cover cap 334 of FIG. 24, and shows the hinged lids, and schematically shows by arrows how liquid can be dispersed on opposite sides of divider wall 388.

Finally, FIG. 27 shows in isolated detail divider wall 388, and the operation of hinged lids 384, 386 and slits 390.

FIGS. 28 through 40 show alternative embodiments for the invention with a further feature that can be optionally advantageously used with the invention. Each of the embodiments in FIGS. 28 through 40 includes the basic operational and structural features of previous embodiments, but adds the ability to dispense fluid from the fluid container externally of the device if desired.

It is therefore to be understood that with respect to storage and caring of contact lenses within the contact lens holder, the providing of fluid to the contact lens holder or holders is similar to that previously described. Additionally, the fluid container, its attachment to the contact lens holder, and the method by which fluid is channeled to the contact lens holder or holders is basically similar to that previously described. Therefore, reference should be taken to the previous description for specific details on these matters.

The following will concentrate on describing the external dispensing feature in its combination with the contact lens holder and fluid container combination.

Specifically referring to FIG. 28, an embodiment 400 according to the present invention is shown in perspective. A lens holder 402 is removably connectable to a fluid container 404. Also similar to the previously described embodiments, a cap or lid 406 is associated with the top of lens holder 402 to provide access to recessed cup chambers 408 and 409 in lens holder 402 (see FIGS. 29 and 30).

Embodiment 400 has an additional feature. A dispensing tip 410 extends from cap 406 and includes a removable tip cap 412. Dispensing tip 410 allows fluid from fluid container 404 to be directed out from embodiment 400 when tip cap 412 is removed. Such dispensing can be done without directing any of the fluid to the recessed chambers 408 in lens holder 402. For whatever reason or use, fluid is always available for external use.

The specifics of embodiment 400 can be more clearly understood with reference to FIGS. 29-34. In FIG. 29, it is shown how embodiment 400 includes distributor head 414 which directs fluid from fluid container 404 into recessed chambers 408 when fluid container 404 is squeezed, or otherwise actuated to deliver fluid to distributor head 414. This is similar to previously described embodiments. Also, cap or lid 406 can contain rings 416 on its bottom surface which mate into the perimeters of recessed chambers 408 to seal those chambers off and prevent fluid from either getting in or getting out when cap 406 is closed down upon lens holder 402.

Cap 406 of lens holder 402 furthermore has a dispensing channel 418 aligned with distributor head 414 when cap 406 is closed. As can be seen in FIG. 30, dispensing channel 418 is in fluid communication with a dispensing bore 420 which terminates in an outer tip opening 422.

As can be easily understood by reference to the drawings, when cap 406 is in an open position, such as in FIG. 29, and embodiment 400 is in a basically upright position, fluid exiting distributor head 414 would fall into recessed chambers 408 of lens holder 402.

However, as shown in FIG. 30, when cap 406 is closed, it blocks off any fluid pathway from distributor head 414 to recessed chambers 408, and instead would present an open pathway through dispensing channel 414, dispensing bore 420, and outer tip opening 422 if tip cap 412 is removed.

Embodiment 400 therefore presents the additional option of being able to dispense fluid from fluid container 404 exteriorly of embodiment 400, when desired.

A further aspect of embodiment 400 can be the inclusion of what will be referred to as a 360° valve 424. Valve 424 is utilized, in embodiment 400, to facilitate efficient and reliable operation of embodiment 400 in either mode of use for obtaining fluid from fluid container 404.

The general operation of 360° valve 424 will first be described; followed by a more detailed discussion of its structure.

As can be seen in FIGS. 30-32, 360° valve 424 consists of the combination structure located within the fluid pathway between fluid container 404 and lens holder 402.

It is to be understood that when fluid is desired to be transferred to recessed chambers 408 of lens holder 402, embodiment 400 is generally to be placed in a substantially upright position; preferably rested on a flat surface in the position shown at FIG. 29 with cap 406 raised to the open position. Embodiment 400 uses what is called a dip tube 426 extending axially through the interior of fluid container 404 towards its bottom end. As with previously described embodiments, fluid container 404 is squeezed around its side wall. Air inside fluid container 404 is displaced forcing fluid up dip tube 426 through distributor head 414 into recessed chambers 404. A release of the side wall of container 404 allows the air to fill container 404 up again and fluid retracts down dip tube 426. It is to be understood that generally the term dip tube 426 will refer to the entire fluid pathway between distributor head 414 and the lower end of the tube extending towards the bottom of fluid container 404. In these embodiments dip tube 426 is not made of one piece, however.

If embodiment 400 was used only for this purpose, 360° valve 424 would not be needed. However, with the addition of dispensing tip 400, many times it is desired to direct fluid from fluid container 404 to an external location, and to do it with some precision. This normally would require embodiment 400 to be inverted or substantially inverted so that the dispensing tip 410 can be pointed directly towards its intended target, which is generally some item or container on a counter or the like.

In such a situation, fluid in fluid container 404 would, of course, flow to the mouth 428 of fluid container 404, leaving the lower end of dip tube 426 exposed to only air. It would not be very easy, if not being impossible, to transfer fluid through the entire length of dip tube 426.

Therefore, 360° valve 424 provides an alternative inlet into dip tube 426. As can be seen in FIG. 30, a ball 430 is normally seated in valve seat 432 when fluid container 404 is in an upright position. Valve seat 432 defines the alternative opening 434 into dip tube 426.

When embodiment 400 is substantially inverted, ball 430 falls out of valve seat 432 exposing opening 434. Squeezing the side wall of fluid container 404 causes air to be displaced downwardly forcing fluid through opening 434 into the upper portion 436 of dip tube 426 and through distributor head 414, and out dispensing channel 418, dispensing bore 420, and outer tip opening 422, to the external target area. Of course, cap 406 is in its closed position, blocking off any fluid pathway to recessed chambers 408, and tip cap 412 is removed.

Thus, this embodiment utilizing the dip tube 426, allows efficient and reliable operation in either mode for either function.

FIG. 30 also shows how lens holder 402 can be snapped onto fluid container 404 around its mouth 428 by utilizing mating beveled flanges 438 and 440 respectively. FIG. 30 also shows how tip cap 412 can include a bead 442 which matably fits in outer tip opening 422 of dispensing tip 410 to frictionally attach to that position. It is to be understood that cap 406 can also have some sort of snap flange around its perimeter to retain it in a closed position on lens holder 402.

In embodiment 400, the lower portion 444 of dip tube 426 comprises a simple tube which can be pushed on to end 446 of the upper portion 436 of dip tube 426. Upper portion 436 can in turn be pushed into a receiving bore 448 in lens holder 402.

The 360° valve 424 simply comprises a part of upper portion 436 of dip tube 426. It is especially noted that it includes an extended portion 450 laterally of the longitudinal axis 452 of the entire dip tube 426. The pathway with least resistance through the entire length of dip tube 426 is thus along the longitudinal axis 452.

It can further be seen that the retainer member 454 extending laterally on the exterior of upper portion 436 of dip tube 426 functions to retain ball 430 when it is unseated from valve seat 432. Container member 454 is basically a U-shaped member having its legs extending from their free ends laterally outwardly from upper portion 436 and dip tube 426. The interior open area of retainer member 454 is smaller in any direction than the diameter of ball 430 so that ball 430 cannot pass by retainer member 454 in a direction parallel to the longitudinal axis 452 of dip tube 426. Additionally, retainer member 454 is spaced upwardly from valve seat 432 so that its adjacent edge is a distance less than the diameter of ball 430, so that ball 430 cannot escape laterally between retainer member 454 and valve seat 432.

It is to be understood that valve seat 432 is beveled. When embodiment 400 is in an upright position and the side wall of fluid container 404 is squeezed inwardly, the air pressure works to urge the ball 430 into a tighter seal in valve seat 432.

When embodiment 400 is substantially inverted, air pressure will act to push ball 430 out of valve seat 432 where it will be retained by retaining member 454. It will be noted that when substantially inverted, although fluid has to flow through valve seat 432 and basically make a 180° turn through upper portion 436 of dip tube 426 to dispensing tip 410, this offers the path of least resistance as air pressure is both forcing fluid through valve seat 432 as well as pushing against any fluid wishing to enter lower portion 444 of dip tube 426.

FIGS. 31 and 32 show in more detail the construction of 360° valve 424 and its relationship to dip tube 426. It is also noted that in embodiment 400, 360° valve 424 is basically positioned within mouth 428 of fluid container 404. Ball 430 also in the preferred embodiment is made of stainless steel so that it has a higher density than fluids used with fluid container 404.

FIGS. 33 and 34 show in cross section both possible modes for embodiment 400 with respect to alternative fluid routes or pathways. FIG. 33 shows embodiment 400 in the upright position with cap 406 raised. 360° valve 424 has ball 430 seated in valve seat 432, and fluid would flow through the entire length of dip tube 426 into recessed chambers 408 of lens holder 402.

FIG. 34 depicts the inverted embodiment 400 with tip cap 412 removed and cap 406 closed. Ball 430 is unseated from valve seat 432, and fluid would flow from fluid container 404 up through valve seat 432 (as inverted) and then out of upper portion 436 of dip tube 426, distributor head 414, dispensing channel 418, dispensing bore 420, and outer tip opening 422, to an external target location.

It is to be understood that in FIG. 34, contact lenses and fluid could be previously contained within recessed chambers 408, if desired, or they could be empty.

FIGS. 35-37 show a similar two mode embodiment 460, with an additional feature. Embodiment 460 operates like embodiment 400 and allows fluid flow from fluid container 404 either to recessed chambers 408 of lens holder 402, or out dispensing tip 464. However, in embodiment 460, cap 462 and dispensing tip 464 differ in the following ways.

Unlike embodiment 400, in embodiment 460 dispensing tip 464 is a separate component which is rotatably mounted in the upper surface 466 of cap 462. Additionally, dispensing tip 464 has a dispensing channel 468 which is a narrow-in-width rectangularly shaped void.

In essence, distributor head 414 has orifices 470 and 472 which are positioned 180° from one another on opposite sides of distributor head 414. Orifices 470 and 472 are substantially narrow in width. Embodiment 460 therefore allows dispension of fluid from dispensing tip 464 only when dispensing channel 468 is rotated to be in alignment with orifices 470 and 472. When rotated out of alignment, the fluid pathway is blocked.

This arrangement gives the added security for blocking fluid flow in addition to that supplied by tip cap 412.

As can be seen in FIGS. 35-37, a wide bottom flange 474 of dispensing tip 464 is seated in circular groove 476 in the top of cap 462. Groove 476 has inner facing beveled inner and outer side edges 478 and 480 which mate with beveled side edges 482 and 484 of flange 474. This allows dispensing tip 464 to be retained in cap 462 but with the ability to rotate.

Because rotation of dispensing tip 464 need only be through approximately 90°, a 90°-in-arc groove 486 (see FIG. 37) in the bottom of circular groove 476 receives pin 488 extending downwardly from the bottom side of bottom flange 474 of dispensing tip 464. (See FIG. 36). At one extreme of groove 486, dispensing channel 468 is aligned with orifices 470 and 472 of distributor head 414 (as shown in FIG. 37). At the other extreme, dispensing channel 468 is turned 90° from orifices 470 and 472 blocking fluid flow as previously described.

It is to be understood that indicia can be included on cap 462 to inform the user of the positions for opening fluid flow through dispensing tip 464, or closing such fluid flow.

FIGS. 38-40 show another embodiment having a two-mode capability. Like embodiments 400 and 460, embodiment 490 can supply fluid from fluid container 404 to recessed chambers 408, or dispense it externally. Embodiment 490, as with embodiments 400 and 460, also can include 360° valve 424.

The major difference in embodiment 490 is the relative positioning of dispensing tip 492. Unlike previous embodiments, dispensing tip 492 is snap locked around mouth 428 of fluid container 404. Dispensing bore 496 of dispensing tip 492 is positioned directly above the upper end of the upper portion 436 of dip tube 426 and in fluid communication therewith.

As shown in FIG. 39, lens holder 500 is mountable upon the upper surface of dispensing tip 492. It is to be understood that by means well known within the art, lens holder 500 can contain bores and apertures which mate with portions of dispensing tip 492 to allow removable securement of lens holder 500 to dispensing tip 492 and fluid container 404. One example is the use of resilient materials which frictionally or with a clamping action grip portions of dispensing tip 492, but which can be easily removed.

As further shown in FIGS. 38-40, cap 502 on lens holder 500 simply opens and closes to block fluid passage from distributor head 414 to recessed chambers 408. In the first mode where embodiment 490 is used as a lens holder and treatment holder for lenses, lens holder 500 would be connected to dispensing tip 490 and fluid container 404 as shown in FIG. 39. Cap 502 would then be closed to contain and isolate the contents of recessed chambers 408, and opened to allow fluid to pass through dip tube 426, dispensing bore 496 of dispensing tip 492, bore 504 in lens holder 500 and through the orifices in distributor head 414 into recessed chambers 408.

In a second mode, where fluid is dispensed directly out of the fluid container 404 to an external location. As can be seen in FIG. 40, similar to FIG. 34 with respect to embodiment 400, the dispensing of fluid is generally done with embodiment 490 substantially inverted. 360° valve 424 is utilized to work in the same way as previously described. By simply removing lens holder 500 from dispensing tip 492, dispensing tip 492 is exposed to allow fluid dispension. Cap 502 functions to retain the contents in recessed chambers 408 and lens holder 500 can be used as a separate but attachable lens holder.

It can be seen that as with other embodiments, embodiment 490 presents a multifunction, flexible system where a reservoir of fluid can be always available for contact lens care and even other uses.

It will be appreciated that the present invention can take many forms and embodiments. The true essence and spirit of this invention are defined in the appended claims, and it is not intended that the embodiments of the invention presented herein should limit the scope thereof. It can therefore be seen that the invention achieves at least all of its stated objectives.

What is claimed is:

1. A multifunction means for storing and caring for contact lenses, and for optionally dispensing fluids comprising:

a first container means for containing and supporting at least one contact lens, and for receiving and containing, as desired, a fluid used in contact lens care, the first container means including an enclosable fluid-tight chamber and a cap means movable between closed and open positions to enclose the first container means and allow insertion and removal of the contact lens;

connection means for removably securing the first container means to a second container means; and conduit means providing fluid communication from the second container means to the first container means and to a dispensing tip means having an outer end opening which can dispense fluid externally of the multifunction means; and the cap means blocking fluid communication between the first and second container means in the closed position and allowing selective dispensing of fluid from the second container externally of the first container means and the second container means through the dispensing tip means.

2. The multifunction means of claim 1 further comprising a valve means operatively positioned in the conduit means, the valve means including an outlet from the conduit means, a stopper means movable into and out of sealing position in the outlet means, and allows fluid flow through the conduit and not out of the outlet when seated in the outlet, but allows fluid flow into the conduit through the outlet when unseated from the outlet.

3. The multifunction means of claim 2 wherein the valve means is configured so that the stopper is seated in the outlet when the multifunction means is in a substantially upright position, but is unseated from the outlet when the multifunction means is moved away from a substantially upright position.

4. The multifunction means of claim 1 wherein the first container means comprises a bottle having resilient side walls so that the bottle can be squeezed to transfer the fluid to the fluid conduit.

5. The multifunction means of claim 1 wherein the fluid conduit includes a dip tube means extending generally to the bottom of the first container means.

6. The multifunction means of claim 1 wherein the dispensing tip means includes a closure means.

7. The multifunction means of claim 1 wherein the dispensing tip means is contained within the cap means.

8. The multifunction means of claim 1 wherein the cap means includes a blocking means to interrupt the fluid communication between the first and second container means.

9. The multifunction means of claim 1 wherein the cap means includes a fluid channel in communication with the outer end opening of the dispensing tip means.

10. The multifunction means of claim 1 wherein the cap means blocks the fluid communication between the first and second container means and the closed position, and can allow selective dispensing of fluid from the second container through the dispensing tip means in a third position.

11. The multifunction means of claim 10 wherein the third position is a rotation of the cap means so that a channel means is aligned with the conduit means, and is in fluid communication with the outer end opening of the dispensing tip means.

12. The multifunction means of claim 12 wherein the third position is removal of the first container means, including the cap means, from the multifunction means.

13. The multifunction means of claim 1 wherein the dispensing tip means is positioned in the conduit means between the second and first container means.

14. The multifunction means of claim 13 wherein the cap means is moved to the open position to allow fluid from the second container to communicate with the first container means to clean contact lenses.

15. The multifunction means of claim 13 wherein the cap means is moved to a closed position to block the fluid from entering or leaving the first container means to allow the contact lenses to be stored or cleaned.

16. The multifunction means of claim 13 wherein the first container means is removed from the second container means to allow fluid from the second container means to be dispensed from the dispensing tip means to an external position.

17. A system for storing and caring of contact lenses, and alternatively allowing dispensing of fluid used in caring for contact lenses comprising:
a contact lens holder means for removably supporting and containing fluids for at least one contact lens;
a fluid conduit means positioned in the contact lens holder means for conducting fluid to the contact lens holder means;
an interchangeable fluid container means removably attachable to the fluid conduit means and contact lens holder means for putting the contact lens holder means into selective fluid communication with the fluid used in the care of contact lenses; and
dispensing tip means in fluid communication with the fluid conduit means, the dispensing tip means when in a first position relative to the fluid conduit means allowing the direction of fluid from the fluid container means out a dispensing tip and externally of the contact lens holder means.

18. The system of claim 17 wherein the dispensing tip means blocks fluid communication to the first container means in a second position.

19. The system of claim 18 wherein the dispensing tip means intercepts fluid blocked and directs it out the dispensing tip end when in the second position.

20. The system of claim 19 wherein the dispensing tip means is incorporated into a cap means which encloses the contact lens holder means in a closed position.

21. The system of claim 19 further comprising a 360° valve means operatively positioned in the fluid conduit means for allowing fluid flow only through the fluid conduit means when the system is in a substantially upright position, but allowing the fluid to enter the fluid conduit through a side opening when the system is substantially in an inverted position.

22. The system of claim 17 wherein the dispensing tip means is operatively positioned in line with the fluid conduit means.

23. The system of claim 22 wherein the fluid is allowed to pass through the dispensing tip means to the first container means when the contact lens holder means is in fluid communication with the fluid used in the care of contact lenses.

24. The system of claim 22 wherein the fluid used in the care of contact lenses can be dispensed to an external position upon removal of the contact lens holder means.

25. A means for selectively storing and caring for contact lenses and dispensing of fluid used in the care of contact lenses comprising:
a base member including one or more cup shaped chambers defined by fluid-tight walls into which can be placed the contact lens and fluid used in the care of contact lenses, a cap securable to the base member which can adjustably cover at least a portion of each chamber to prevent loss of a contact lens or fluid from the chamber during storage or caring for the contact lens, a tubular duct in the base member having a first open end and a second open end, a distributor member connected to the first open end of the duct for distributing fluid passing through the duct to each chamber;
connection means on the base for interchangeable attachment of a fluid container to the base member so that the second end of the duct is in fluid communication with any fluid in the fluid container;
dispensing tip means included in the cap and having dispensing channels which can be brought into selective fluid communication with the distributor member, a dispensing bore terminating in an open dispensing tip end, and a dispensing tip cap removable over the open dispensing tip; and
the cap means blocking distribution of fluid to any chamber in the base member when covering the chambers, but allowing fluid through the dispensing channel, dispensing bore, and outer end, when the tip end cap is removed and the dispensing channel is aligned in fluid communication with the distributor member.

26. A means for selectively storing and caring for contact lenses and dispensing of fluid used in the care of contact lenses comprising:
a base member including one or more cup shaped chambers defined by fluid-tight walls into which can be placed the contact lens and fluid used in the care of contact lenses, a cap securable to the base member which can adjustably cover at least a portion of each chamber to prevent loss of a contact lens or fluid from the chamber during storage or caring for the contact lens, a tubular duct in the base member having a first open end and a second open end, a distributor member connected to the first open end of the duct for distributing fluid passing through the duct to each chamber;

connection means on the base for interchangeable attachment of a fluid container to the base member so that the second end of the duct is in fluid communication with any fluid in the fluid container;

a dispensing tip means operatively positioned in fluid communication with the tubular duct of the base member and connected to the fluid container between the fluid container and the base member, a dispensing tip means including a dispensing bore terminating in an outer dispensing tip end, the dispensing tip means channeling fluid to the tubular duct when the base member is attached, but allowing dispensing of fluid from the fluid container to an external location upon removal of the base member.

27. A multifunction means for storing and treating contact lens with a fluid, and for externally dispensing a fluid comprising:

a contact lens holding case including one or more cup shaped chambers for holding contact lenses, a removable cover to substantially enclose the chamber;

a fluid container for fluid used in contact lens care having an access opening;

means for connecting the holding case to the fluid container;

fluid conduit means extending from the interior of the container to the holding case for conducting fluid from the fluid container to the holding case;

distributor means associated with the holding case and in fluid communication with the conduit having at least one passageway for directing fluid from the conduit of the fluid container to the chambers, and including a passageway in fluid communication with a dispensing tip means for dispensing fluid from the fluid chamber externally of the contact lens holding case and the fluid container; and blocking means associated with the cover which block fluid from entering the chambers from the passageway of the distributor when the cover is closed.

28. The means of claim 27 wherein the fluid container is squeezable and made of a flexible resilient material.

29. The means of claim 28 further comprising a valve means for assisting in operation of the means regardless of the orientation of the means, the valve means having a ball member seatable into a valve seat opening in the fluid conduit, and including a retaining means for retaining the ball means in close proximity to the seat when displaced from the seat, the ball means allowing air pressure to seat the ball means within the seat opening when fluid is below the valve means, and the ball means being displaced from the seat opening when fluid is generally above the valve means.

30. A multifunction means for storing and caring for contact lenses, and for optionally dispensing fluids comprising:

a first container means for containing and supporting at least one contact lens, and for receiving and containing, as desired, a fluid used in contact lens care, the first container means including an enclosable fluid-tight chamber and a cap means movable between open and closed position to enclose the first container means and allow insertion and removal of the contact lens;

connection means for removably securing the first container means to a second container means;

conduit means providing fluid communication from the second container means to the fist container means and to a dispensing tip means having an outer end opening which can dispense fluid externally of the multifunction means; and a valve means operatively positioned in the conduit means, the valve means including an outlet from the conduit means, a stopper means movable into and out of sealing position in the outlet means, and allows fluid flow through the conduit and not out of the outlet when seated in the outlet, but allows fluid flow into the conduit through the outlet when unseated from the outlet.

31. A multifunction means for storing and caring for contact lenses, and for optionally dispensing fluids comprising:

a first container means for containing and supporting at least one contact lens, and for receiving and containing, as desired, a fluid used in contact lens care, the first container means including an enclosable fluid-tight chamber and a cap means movable between open and closed position to enclose the first container means and allow insertion and removal of the contact lens;

connection means for removably securing the first container means to a second container means;

conduit means providing fluid communication from the second container means to the fist container means and to a dispensing tip means having an outer end opening which can dispense fluid externally of the multifunction means; and the cap means including a fluid channel in fluid communication with the outer end opening of the dispensing tip means.

32. A multifunction means for storing and caring for contact lenses, and for optionally dispensing fluids comprising:

a first container means for containing and supporting at least one contact lens, and for receiving and containing, as desired, a fluid used in contact lens care, the first container means including an enclosable fluid-tight chamber and a cap means movable between open and closed position to enclose the first container means and allow insertion and removal of the contact lens;

connection means for removably securing the first container means to a second container means;

conduit means providing fluid communication from the second container means to the fist container means and to a dispensing tip means having an outer end opening which can dispense fluid externally of the multifunction means; and the cap means blocking the fluid communication between the first and second container means in the closed position, and allowing selective dispensing of fluid from the second container through the dispensing tip means in a third position, the third position being a rotation of the cap means so that a channel means is aligned with the conduit means, and is in fluid communication with the outer end opening of the dispensing tip means.

33. A multifunction means for storing and treating contact lens with a fluid, and for externally dispensing a fluid comprising:

a contact lens holding case including one or more cup shaped chambers for holding contact lenses, a removable cover to substantially enclose the chamber;

a fluid container for fluid used in contact lens care having an access opening;

means for connecting the holding case to the fluid container;

fluid conduit means extending from the interior of the container to the holding case for conducting fluid from the fluid container to the holding case;

distributor means associated with the holding case and in fluid communication with the conduit having at least one passageway for directing fluid from the conduit of the fluid container to the chambers, including a passageway and in fluid communication with a dispensing tip means for dispensing fluid from the fluid chamber externally of the contact lens holding case and the fluid container;

blocking means associated with the cover which block fluid from entering the chambers from the passageway of the distributor when the cover is closed;

the fluid container being squeezable and made of a flexible resilient material; and a valve means for assisting in operation of the means regardless of the orientation of the means, the valve means having a ball member seatable into a valve seat opening in the fluid conduit, and including a retaining means for retaining the ball means in close proximity to the seat when displaced from the seat, the ball means allowing air pressure to seat the ball means within the seat opening when fluid is below the valve means, and the ball means being displaced from the seat opening when fluid is generally above the valve means.

* * * * *